United States Patent
Goswami et al.

(10) Patent No.: US 11,938,212 B2
(45) Date of Patent: Mar. 26, 2024

(54) SKIN CARE COMPOSITIONS

(71) Applicant: Colgate-Palmolive Company, New York, NY (US)

(72) Inventors: Sayantani Goswami, Edison, NJ (US); Thomas Boyd, Metuchen, NJ (US); Qiang Wu, Hillsborough, NJ (US); Jin Namkoong, High Bridge, NJ (US); Aaron Cohen, New Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 18/194,482

(22) Filed: Mar. 31, 2023

(65) Prior Publication Data

US 2023/0320969 A1    Oct. 12, 2023

Related U.S. Application Data

(60) Provisional application No. 63/432,356, filed on Dec. 13, 2022, provisional application No. 63/432,358, filed on Dec. 13, 2022, provisional application No. 63/328,857, filed on Apr. 8, 2022.

(51) Int. Cl.

| | | |
|---|---|---|
| *A61K 8/67* | (2006.01) | |
| *A61K 8/14* | (2006.01) | |
| *A61K 8/35* | (2006.01) | |
| *A61K 8/44* | (2006.01) | |
| *A61K 8/49* | (2006.01) | |
| *A61K 8/73* | (2006.01) | |
| *A61Q 17/04* | (2006.01) | |
| *A61Q 19/08* | (2006.01) | |

(52) U.S. Cl.
CPC ............... *A61K 8/678* (2013.01); *A61K 8/14* (2013.01); *A61K 8/35* (2013.01); *A61K 8/44* (2013.01); *A61K 8/447* (2013.01); *A61K 8/4913* (2013.01); *A61K 8/4946* (2013.01); *A61K 8/675* (2013.01); *A61K 8/676* (2013.01); *A61K 8/73* (2013.01); *A61K 8/735* (2013.01); *A61Q 17/04* (2013.01); *A61Q 19/08* (2013.01)

(58) Field of Classification Search
CPC ........ A61K 8/678; A61K 8/44; A61K 8/4913; A61K 8/675; A61K 8/676; A61K 8/73; A61Q 17/04; A61Q 19/08
See application file for complete search history.

(56) References Cited

U.S. PATENT DOCUMENTS

| | | | |
|---|---|---|---|
| 8,529,925 B2 | 9/2013 | Alexiades-Armenakas | |
| 9,713,604 B2 | 7/2017 | Dreher | |
| 10,045,925 B2 | 8/2018 | Powell | |
| 2014/0147525 A1 | 5/2014 | De Paula | |
| 2015/0164766 A1* | 6/2015 | Krueger | A61K 8/44 424/70.13 |
| 2016/0374933 A1* | 12/2016 | Tanner | A61Q 19/007 424/401 |

FOREIGN PATENT DOCUMENTS

| | | |
|---|---|---|
| CN | 106038361 | 10/2016 |
| CN | 114224779 | 3/2022 |
| EP | 1994923 | 11/2008 |
| WO | 2001/000162 | 1/2001 |
| WO | 2006/124992 | 11/2006 |

OTHER PUBLICATIONS

Naya (Hyaluronic Acid Explained, Sep. 19, 2021 https://web.archive.org/web/20210919224549/https://nayaglow.com/blogs/news/hyaluronic-acid-explained (Year: 2021).*
Botica Comercial Farmaceutica, 2022, "Invisible Foundation SPF60," Mintel Database GNPD AN:9325230.
C'bon Cosmetics, 2021, "Vital Serum", Mintel Database GNPD AN: 9177072.
Chuan Mei Enterprise, 2021, "Energy Boosting Essence Cream", Mintel Database GNPD AN: 8658935.
International Search Report and the Written Opinion of the International Searching Authority issued in International Application PCT/US2023/017163 dated Aug. 3, 2023.
International Search Report and Written Opinion of the International Searching Authority in International Application No. PCT/US2023/017133, dated Oct. 4, 2023.
Kendo, 2022, "Strength Trainer Peptide Boost," Mintel Database GNPD AN:9285422.
Laboratoires Filorga, 2012, "Hydra-Filler Pro-Youth Boosting Moisturizer", Mintel Database GNPD AN: 1859499.
NY Derm, 2011, "High Performance Anti-Aging Cream", Mintel Database GNPD AN: 1649146.

* cited by examiner

*Primary Examiner* — Anna R Falkowitz

(57) ABSTRACT

Disclosed herein are skin care compositions, comprising vitamin E (e.g., alpha-tocopherol), a thiourea derivative of histidine (e.g., ergothioneine), a vitamin B3 compound (e.g., niacinamide) and/or a pyrrolidone carboxylic acid and/or a salt thereof (e.g., sodium PCA) as well as to methods of using these compositions.

10 Claims, 2 Drawing Sheets

SKIN CARE COMPOSITIONS

CROSS-REFERENCE TO RELATED APPLICATIONS

This application claims the benefit of priority from U.S. Provisional Application No. 63/432,358, filed Dec. 13, 2022; from U.S. Provisional Application No. 63/432,356, filed Dec. 13, 2022; and from U.S. Provisional Application No. 63/328,857, filed Apr. 8, 2022, the contents of which are hereby incorporated herein in their entireties, for all purposes.

BACKGROUND

Reactive oxygen species (ROS) are free radicals that can react with various cellular proteins in the skin, for example, collagen, elastin and glycosaminoglycans. ROS causes cross-linking of collagen and elastin resulting in wrinkles and decreasing the skin's ability to repair itself. Thus, the skin damage caused by ROS can contribute to the physiology of aging or lead to skin disorders. Antioxidants can scavenge and decrease the excessive ROS produced and mitigate its damage to the cells of different tissues, including skin.

Furthermore, in the field of skin health, recent consumer trends are requiring products be as simple as possible but still provide acceptable skin health benefits that consumers have grown accustomed to in products with a number of ingredients. However, when using fewer ingredients, there is more of an emphasis on maximizing the results and efficacy of each ingredient in order to delivery anti-oxidant and skin health benefits to a consumer.

Accordingly, there is a need for a skin health product that is simple but that can also provide, or exceed, the skin health benefits seen in products that contain numerous ingredients that claim to have skin health benefits.

BRIEF SUMMARY

In one aspect, the inventors have surprisingly discovered that skin care compositions comprising a combination of vitamin E (e.g., alpha-tocopherol) and a thiourea derivative of histidine (e.g., ergothioneine) can be combined with vitamin $B_3$ (e.g., niacinamide) and/or sodium pyrrolidone carboxylic acid, in various ratios and amounts, in order to provide unexpectedly enhanced reduction and inhibition of cellular damage caused or related to free radicals (ROS) and environmental damage (by UV rays).

In one aspect, the skin care compositions comprise pyrrolidone carboxylic acid ("PCA") and/or a salt thereof (e.g. sodium PCA) which is believed to be a hygroscopic substance, readily attracting moisture from the air, and which can provide hydration in order to help retain the moisture in the skin. In this aspect, and without being bound by theory, while pyrrolidone carboxylic acid and salts thereof are not believed to act as an antioxidant when incorporated individually, in combination with alpha-tocopherol and ergothioneine in the skin care compositions of the disclosure, it is believed to unexpectedly enhance the ability to of the skin care composition to decrease ROS production. Surprisingly, certain skin care compositions of the present disclose achieve a greater reduction/decrease in ROS production as compared to the expected cumulative reduction of ROS production based on the reduction of ROS production for each of the compounds assessed individually. ROS measurement in this aspect includes detection and measurement of free radicals in biological systems.

In still another aspect, Niacinamide/Vitamin B3 can function individually to improve barrier function of the skin. However, Niacinamide/Vitamin B3, in combination with alpha-tocopherol and ergothioneine, is believed to unexpectedly enhance the ability to act as an antioxidant by causing a greater decrease in the ROS production than the decrease observed for each of the compounds individually. ROS measurement includes detection and measurement of free radicals in biological systems.

Further areas of applicability of the present disclosure will become apparent from the detailed description provided hereinafter. In some aspects, the formulations of the disclosure can be used in methods to: revitalize of skin cells, enhance cellular energy in skin cells (e.g., dermal cells), reduce or inhibit cellular damage related to reactive oxygen species and/or UV light, and to detoxify skin cells.

It should be understood that the detailed description and specific examples, while indicating some typical aspects of the disclosure, are intended for purposes of illustration only and are not intended to limit the scope of the disclosure.

DETAILED DESCRIPTION

Figure 1:
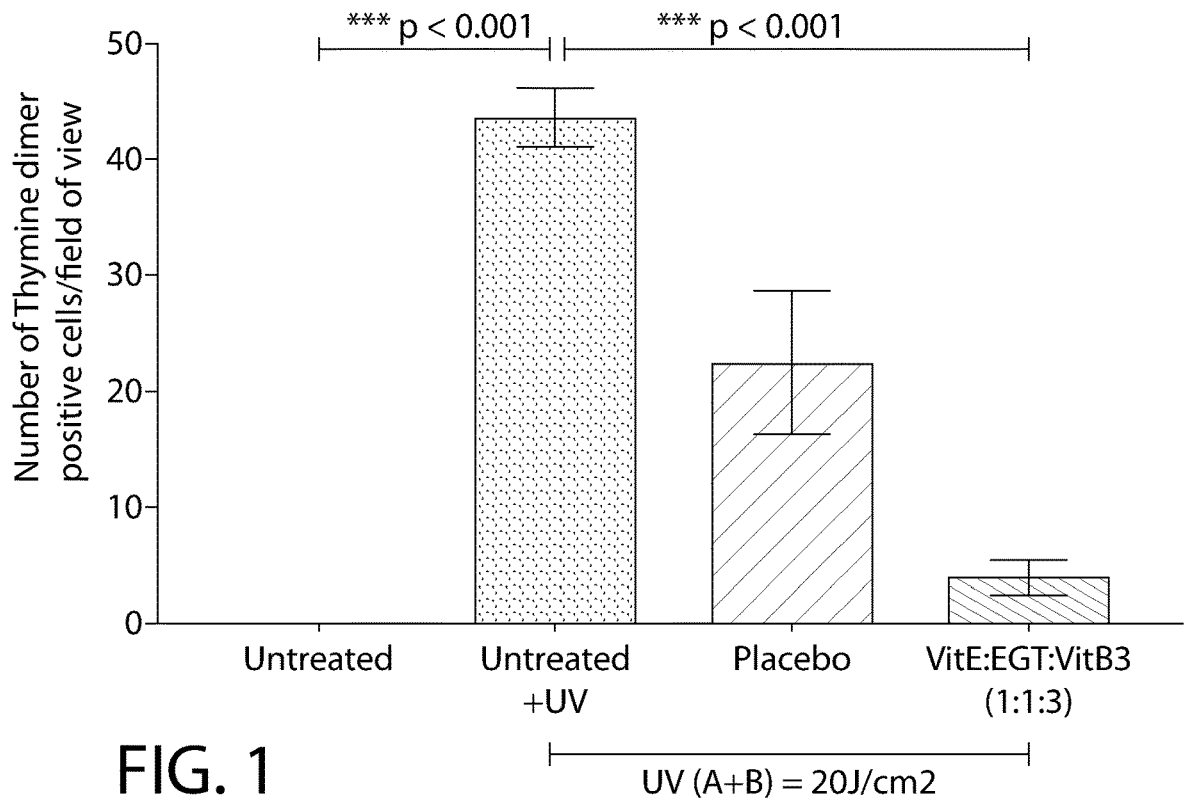
FIG. 1 is a bar graph depicting the number of thymine dimer positive cells after application of a non-limiting exemplary compositions and exposure to UV in accordance with an aspect of the invention.

The following description of various typical aspect(s) is merely exemplary in nature and is in no way intended to limit the disclosure, its application, or uses.

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight relative to the total composition. Unless specified otherwise, the amounts given are based on the active weight of the material.

In one aspect, the disclosure relates to antioxidant skin care compositions that effectively treat, prevent and/or reduce free radical damage to the skin of a user. It has been found that the addition of pyrrolidone carboxylic acid and/or sodium PCA and/or Niacinamide/Vitamin B3 in combination with both vitamin E (e.g., alpha-tocopherol) and a thiourea derivative of histidine (e.g., ergothioneine) can provide unexpectedly enhanced protection to the skin from the damage incurred by reactive oxygen species.

The present invention provides, in one aspect, a skin care composition (Composition 1.0), comprising vitamin E (e.g., alpha-tocopherol), a thiourea derivative of histidine (e.g., ergothioneine), a vitamin B3 compound (e.g., niacinamide) and optionally a pyrrolidone carboxylic acid and/or a salt thereof (e.g., sodium PCA).

For example, the disclosure includes:

1.1. The skin care composition of Composition 1.0, wherein vitamin E is vitamin E acetate or vitamin E succinate, or vitamin E acetate.

1.2. Any of the preceding compositions wherein the vitamin E is selected from the group consisting of alpha-tocopherol, beta-tocopherol, gamma-tocopherol, delta-tocopherol, alpha-tocotrienol, beta-tocotrienol, gamma-tocotrienol, delta-tocotrienol, tocopherol acetate, tocopherol phosphate, natural extracts enriched in vitamin E derivatives, and combinations thereof.

1.3. The preceding composition wherein the vitamin E is alpha-tocopherol or topically acceptable salts thereof.

1.4. Any of the preceding compositions, wherein vitamin E is present in an amount of from 0.1% to 5%, e.g., from 0.2% to 2%, or from 0.2% to 1.5%, or from 0.2% to 1.25%, or from 0.2% to 1%, or from 0.2% to 0.9%, or from 0.2% to 0.8%, or from 0.2% to 0.7%, or from 0.2% to 0.6%, or from 0.2% to 0.5%, or from 0.2% to 0.4%, or from 0.2% to 0.3%, or about 2%, or about 1.5%, or about 1.25%, or about 1%, or about 0.9%, or about 0.8%, or about 0.7%, or about 0.6%, or about 0.5%, or about 0.4%, or about 0.3%, or any range or subrange formed therefrom, by weight based on the total weight of the skin care composition.

1.5. Any of the preceding compositions, wherein the thiourea derivative of histidine is ergothioneine.

1.6. The preceding composition, wherein the ergothioneine ("EGT") is present from 0.001% to 2%, e.g., from 0.001% to 2%, or from 0.001% to 1.5%, or from 0.001% to 1.25%, or from 0.001% to 1%, or from 0.001% to 0.5%, or from 0.001% to 0.1%, or from 0.001% to 0.05%, or from 0.001% to 0.01%, or from 0.001% to 0.009%, or from 0.001% to 0.008%, or from 0.001% to 0.0075%, or from 0.001% to 0.007%, or from 0.001% to 0.0065%, or from 0.001% to 0.006%, or from 0.001% to 0.0055%, or from 0.001% to 0.005%, or from 0.001% to 0.0045%, or from 0.001% to 0.004%, or from 0.001% to 0.0035%, or from 0.001% to 0.003%, or from 0.001% to 0.0025%, or from 0.001% to 0.002%, or from 0.001% to 0.0015%, or about 0.0015%, or about 0.002%, or about 0.0025%, or about 0.003%, or about 0.0035%, or about 0.004%, or about 0.0045%, or about 0.005%, or about 0.0055%, or about 0.006%, or about 0.0065%, or about 0.007%, or about 0.0075%, or about 0.008%, or about 0.009%, or about 0.01%, or about 0.05%, or about 0.1%, or about 0.5%, or about 1%, or any range or subrange formed therefrom, by weight based on the total weight of the composition (e.g., wherein the weight refers to the active weight of EGT).

1.7. Any of the preceding compositions wherein the formula of the vitamin B3 comprises:

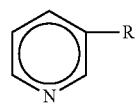

wherein R is —CONH2 (i.e., niacinamide), —COOH (i.e., nicotinic acid) or —CH2OH (i.e., nicotinyl alcohol); a derivative thereof, and/or a salt thereof.

1.8. Any of the preceding compositions wherein the vitamin B3 is selected from the group consisting of nicotinic acid esters, non-vasodilating esters of nicotinic acid, nicotinyl amino acids, nicotinyl alcohol esters of carboxylic acids (e.g., straight-chain or branched chain, cyclic or acyclic, saturated or unsaturated (including aromatic), and substituted or unsubstituted, nicotinic acid N-oxide and niacinamide N-oxide, tocopherol nicotinate and inositol hexanicotinate. Examples of derivatives of niacinamide include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1-C18). Specific examples of such derivatives include nicotinuric acid and nicotinyl hydroxamic acid, which have the following chemical structures:

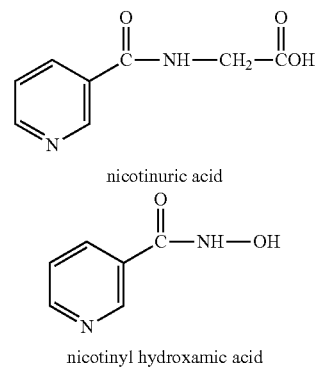

nicotinuric acid nicotinyl hydroxamic acid

Additional derivatives of niacinamide includes nicotinyl alcohol esters, such as nicotinyl alcohol esters of the carboxylic acids, salicylic acid, acetic acid, glycolic acid, palmitic acid and the like Further examples of derivatives of niacinamide include 2-chloronicotinamide, 6-aminonicotinamide, 6-methylnicotinamide, n-methyl-nicotinamide, n,n-diethylnicotinamide, n-(hydroxymethyl)-nicotinamide, quinolinic acid imide, nicotinanilide, n-benzylnicotinamide, n-ethylnicotinamide, nifenazone, nicotinaldehyde, isonicotinic acid, methyl isonicotinic acid, thionicotinamide, nialamide, 1-(3-pyridylmethyl) urea, 2-mercaptonicotinic acid, nicomol, niaprazine, and combinations thereof.

1.9. Any of the preceding compositions, wherein the vitamin B3 compound is present in an amount of from in an amount of from 0.1% to 5%, e.g., from 0.2% to 4.75%, or from 0.2% to 4.5%, or from 0.2% to 4.25%, or from 0.2% to 4%, or from 0.2% to 3.75%, or from 0.2% to 3.5%, or from 0.2% to 3.25%, or from 0.2% to 3%, or from 0.2% to 2.75%, or from 0.2% to 2.5%, or from 0.2% to 2.25%, or from 0.2% to 2%, or from 0.2% to 1.75%, or from 0.2% to 1.5%, or from 0.2% to 1.25%, or about 0.2% to 1%, or about 4.75%, or about 4.5%, or about 4.25%, or about 4%, or about 3.75, or about 3.5%, or about 3.25%, or about 3%, or about 2.75%, or about 2.5%, or about 2.25%, or about 2%, or about 1.75%, or about 1.5%, or about 1.25%, or about 1%, or about 0.5%, or any range or subrange thereof, by weight based on the total weight of the composition. The total amount of vitamin B present in the skin care composition may be from about 0.1 to about 5 wt. %, based on the total weight of the skin care composition.

For instance, the skin care composition may comprise a total amount of vitamin B from about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.7 wt. %; from about 0.3 to about 5 wt. %, about 0.3 to about 4 wt. %, about 0.3 to about 3 wt. %, about 0.1 to about 2 wt. %, about 0.3 to about 1 wt. %, about 0.3 to about 0.7 wt. %; from about 0.5 to about 5 wt. %, about 0.5 to about 4 wt. %, about 0.5 to about 3 wt. %, about 0.5 to about 2 wt. %, about 0.5 to about 1 wt. %, about 0.5 to about 0.7 wt. %; from about 0.7 to about 5 wt. %, about 0.7 to about 4 wt. %, about 0.7 to about 3 wt. %, about 0.7 to about 2 wt. %, about 0.7 to about 1 wt. %; from about 1 to about 5 wt. %, about 1 to about 4 wt. %, about 1 to about 3 wt. %, about 1 to about 2 wt. %, about 1 to about 1.5 wt. %, about 1 to about 1.25 wt. %; from about 1.25 to about 5 wt. %, about 1.25 to about 4 wt. %, about 1.25 to about 3 wt. %, about 1.25 to about 2 wt. %; from about 1.5 to about 5 wt. %, about 1.5 to about 4 wt. %, about 1.5 to about 3 wt. %, about 1.5 to about 2 wt. %; from about 2 to about 5 wt. %, about 2 to about 4 wt. %, about 2 to about 3 wt. %; from about 3 to about 5 wt. %, about 3 to about 4 wt. %, or any range or subrange thereof, based on the total weight of the skin care composition.

1.10. The skin care composition of any of the preceding compositions, wherein the vitamin B3 compound comprises niacinamide.

1.11. The skin care composition of any of the preceding compositions, wherein the skin care composition comprises pyrrolidone carboxylic acid and/or a salt thereof (e.g, sodium PCA). In certain preferred embodiments, the pyrrolidone carboxylic acid and/or a salt thereof comprises L-pyrrolidone carboxylic acid and/or a salt thereof.

1.12. The preceding skin care composition, wherein the pyrrolidone carboxylic acid and/or salt(s) thereof is present from 0.1%-5% by wt. relative to the total composition (e.g., from 0.5%-2%, or from 0.5% to 1.5%, or from 0.5% to 1.25%, or from 0.5% to 1%, or from 0.75% to 1.25% by wt.) (e.g., about 0.5% by wt.) (e.g., about 1% by wt.) (e.g., about 1.5% by wt.) (e.g., about 2% by wt.). In some embodiments, the skin care composition comprises pyrrolidone carboxylic acid and/or salt(s) thereof in an amount from about 0.1 to about 5 wt. %, based on the total weight of the personal care composition. For example, the total amount of the pyrrolidone carboxylic acid and/or salt(s) thereof present in the skin care composition may be from about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.7 wt. %; from about 0.3 to about 5 wt. %, about 0.3 to about 4 wt. %, about 0.3 to about 3 wt. %, about 0.1 to about 2 wt. %, about 0.3 to about 1 wt. %, about 0.3 to about 0.7 wt. %; from about 0.5 to about 5 wt. %, about 0.5 to about 4 wt. %, about 0.5 to about 3 wt. %, about 0.5 to about 2 wt. %, about 0.5 to about 1 wt. %, about 0.5 to about 0.7 wt. %; from about 0.7 to about 5 wt. %, about 0.7 to about 4 wt. %, about 0.7 to about 3 wt. %, about 0.7 to about 2 wt. %, about 0.7 to about 1 wt. %; from about 1 to about 5 wt. %, about 1 to about 4 wt. %, about 1 to about 3 wt. %, about 1 to about 2 wt. %, about 1 to about 1.5 wt. %, about 1 to about 1.25 wt. %; from about 1.25 to about 5 wt. %, about 1.25 to about 4 wt. %, about 1.25 to about 3 wt. %, about 1.25 to about 2 wt. %; from about 1.5 to about 5 wt. %, about 1.5 to about 4 wt. %, about 1.5 to about 3 wt. %, about 1.5 to about 2 wt. %; from about 2 to about 5 wt. %, about 2 to about 4 wt. %, about 2 to about 3 wt. %; from about 3 to about 5 wt. %, about 3 to about 4 wt. %, or any range or subrange thereof, based on the total weight of the skin care composition.

1.13. Any of the preceding skin care compositions, wherein the skin care composition comprises water.

1.14. The preceding skin care compositions, wherein the amount of water is from about 25 to about 96% by wt., based on the total weight of the skin care composition, e.g., about 30% by wt., about 40% by wt., about 50% by wt., about 60% by wt., about 70% by wt., about 80% by wt., about 90% by wt., about 96% by wt., or any range or subrange thereof. For example, the total amount of water present in the skin care composition may be from about 25 to about 96 wt. %, about 40 to about 96 wt. %, about 50 to about 96 wt. %, about 60 to about 96 wt. %, about 70 to about 96 wt. %, about 80 to about 96 wt. %, about 85 to about 96 wt. %; from about 25 to about 90 wt. %, about 40 to about 90 wt. %, about 50 to about 90 wt. %, about 60 to about 90 wt. %, about 70 to about 90 wt. %, about 80 to about 90 wt. %, about 85 to about 90 wt. %; from about 25 to about 85 wt. %, about 40 to about 85 wt. %, about 50 to about 85 wt. %, about 60 to about 85 wt. %, about 70 to about 85 wt. %; from about 25 to about 80 wt. %, about 40 to about 80 wt. %, about 50 to about 80 wt. %, about 60 to about 80 wt. %, about 70 to about 80 wt. %; from about 25 to about 70 wt. %, about 40 to about 70 wt. %, about 50 to about 70 wt. %, about 60 to about 70 wt. %; from about 25 to about 60 wt. %, about 40 to about 60 wt. %, about 50 to about 60 wt. %; from about 25 to about 50 wt. %, about 40 to about 50 wt. %, about 50 to about 50 wt. %, about 60 to about 50 wt. %, or any range or subrange thereof, based on the total weight of the skin care composition.

1.15. Any of the preceding compositions, wherein the composition further comprises a gelling agent, an additional antioxidant, a fragrance, or a combination thereof.

1.16. Any of the preceding compositions, wherein the skin care composition is topically delivered to the skin in the form selected from: a serum, a cream, a moisturizer, a mask, a cleanser, oil, salve, lotion, gel, ointment, paste a facial make-up, a toner, an essence, and a balm (e.g., lip balm).

1.17. Any of the preceding compositions, wherein the composition further comprises an additional vitamin selected from vitamin C (e.g., vitamin C salts and derivatives), vitamin D, vitamin K, and combinations thereof.

1.18. Any of the preceding skin care compositions, wherein the composition comprises one or more amino acids selected from: arginine, lysine, serine, citrulline, ornithine, creatine, histidine, diaminobutanoic acid, diaminoproprionic acid, alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine and salts thereof, and combinations thereof. The skin care composition may include one or more amino acid(s) in an amount from about 0.01 to about 5 wt. %, based on the total weight of the skin care composition. In some embodiments, the skin care composition may include an amino acid in amount from about 0.01 to about 2 wt. %, about 0.01 to about 1.7 wt. %, about 0.01 to about 1.4 wt. %, about 0.01 to about 1.2 wt. %, about 0.01 to about 1 wt. %, about 0.01 to about 0.8 wt. %, about 0.01 to about 0.6 wt. %, about 0.01 to about 0.4 wt. %, about 0.01 to about 0.2 wt. %, about 0.01 to about 0.1 wt. %, about 0.01 to about 0.05 wt. %; from about 0.05 to about 3 wt. %, about 0.05 to about 2 wt. %, about 0.05 to about 1.7 wt. %, about 0.05 to about 1.4 wt. %, about 0.05 to about 1.2 wt. %, about 0.05 to about 1 wt. %, about 0.05 to about 0.8 wt. %, about 0.05 to about 0.6 wt. %, about 0.05 to about 0.4 wt. %, about 0.05 to about 0.2 wt. %, about 0.05 to about 0.1 wt. %; from about 0.1 to about 3 wt. %, about 0.1 to about 2 wt. %, about 0.1 to about 1.7 wt. %, about 0.1 to about 1.4 wt. %, about 0.1 to about 1.2 wt. %, about 0.1 to about 1 wt. %, about 0.1 to about 0.8 wt. %, about 0.1 to about 0.6 wt. %, about 0.1 to about 0.4 wt. %, about 0.1 to about 0.2 wt. %; from about 0.3 to about 3 wt. %, about 0.3 to about 2 wt. %, about 0.3 to about 1.7 wt. %, about 0.3 to about 1.4 wt. %, about 0.3 to about 1.2 wt. %, about 0.3 to about 1 wt. %, about 0.3 to about 0.8 wt. %, about 0.3 to about 0.6 wt. %; from about 0.6 to about 3 wt. %, about 0.6 to about 2 wt. %, about 0.6 to about 1.7 wt. %, about 0.6 to about 1.4 wt. %, about 0.6 to about 1.2 wt. %, about 0.6 to about 1 wt. %; from about 1 to about 3 wt. %, about 1 to about 2 wt. %, about 1 to about 1.7 wt. %, about 1 to about 1.4 wt. %, about 1 to about 1.2 wt. %; from about 1.5 to about 3 wt. %, about 1.5 to about 2 wt. %, about 2 to about 3 wt. %, or any range or subrange thereof, based on the total weight of the skin care composition.

1.19. The total amount of amino acid(s) present in the skin care composition may be from about 0.1 to about 7 wt. %, based on the total weight of the skin care composition. For example, the total amount of amino acid(s) in the skin care composition may be from about 0.1 to about 6 wt. %, about 0.1 to about 5 wt. %, about 0.1 to about 3 wt. %, about 0.1 to about 2 wt. %, about 0.1 to about 1.7 wt. %, about 0.1 to about 1.4 wt. %, about 0.1 to about 1.2 wt. %, about 0.1 to about 1 wt. %, about 0.1 to about 0.8 wt. %, about 0.1 to about 0.6 wt. %, about 0.1 to about 0.4 wt. %, about 0.1 to about 0.2 wt. %; from about 0.3 to about 7 wt. %, about 0.3 to about 5 wt. %, about 0.3 to about 3 wt. %, about 0.3 to about 2 wt. %, about 0.3 to about 1.7 wt. %, about 0.3 to about 1.4 wt. %, about 0.3 to about 1.2 wt. %, about 0.3 to about 1 wt. %, about 0.3 to about 0.8 wt. %, about 0.3 to about 0.6 wt. %; from about 0.6 to about 7 wt. %, about 0.6 to about 5 wt. %, about 0.6 to about 3 wt. %, about 0.6 to about 2 wt. %, about 0.6 to about 1.7 wt. %, about 0.6 to about 1.4 wt. %, about 0.6 to about 1.2 wt. %, about 0.6 to about 1 wt. %; from about 1 to about 7 wt. %, about 1 to about 5 wt. %, about 1 to about 3 wt. %, about 1 to about 2 wt. %, about 1 to about 1.7 wt. %, about 1 to about 1.4 wt. %, about 1 to about 1.2 wt. %; from about 1.5 to about 7 wt. %, about 1.5 to about 5 wt. %, about 1.5 to about 3 wt. %, about 1.5 to about 2 wt. %, from about 2 to about 7 wt. %, about 2 to about 5 wt. %, about 2 to about 3 wt. %; from about 3 to about 7 wt. %, about 3 to 5 wt. %, about 4 to about 7 wt. % about 4 to 6 wt. %, or any range or subrange thereof, based on the total weight of the skin care composition.

1.20. The preceding skin care composition, wherein the composition comprises taurine, arginine and glycine. The preceding skin care composition, wherein the taurine:arginine:glycine are in a weight ratio of (1.5-69):(0.5-40):(0.5-1.5), respectively. For instance, the skin care composition may be formulated to have a weight ratio of taurine to arginine to glycine (taurine:arginine:glycine) from about 85:45:1 to about 45:24:1. In some embodiments, the skin care composition has a weight ratio of taurine to arginine to glycine from about 80:42:1 to about 50:30:1; from about 75:40:1 to about 55:29:1; from about 70:37:1 to about 60:31:1, or any range or subrange thereof.

1.21. The preceding skin care composition, wherein the taurine:arginine:glycine are in a weight ratio of about (65):(34):(1), respectively.

1.22. Any of the preceding skin care compositions, wherein the skin care composition comprises an additional ingredient selected from carnosine, cica (asiaticoside), hyaluronic acid and salts thereof (e.g., sodium hyaluronate), magnesium sulfate, saccharide isomerate, a keto-carotenoid (e.g., astaxanthin), nicotinamide adenine dinucleotide (NAD), and a combination of two or more thereof.

1.23. Any of the preceding skin care compositions further comprising a topically acceptable carrier.

1.24. Any of the preceding skin care compositions wherein one or more ingredients are encapsulated in a delivery vesicle (e.g., a multilamellar vesicle ("MLV")).

1.25. The preceding skin care composition, wherein the MLV comprises liposome structuring amounts of polyglyceryl-10 dioleate and at least one of polyglyceryl-10 dilinoleate or polyglyceryl-10 dipalmitate in a weight ratio of polyglyceryl-10 dioleate to the at least one of polyglyceryl-10 dilinoleate or polyglyceryl-10 dipalmitate of from 300:1 to 5:1.

1.26. Any of the preceding skin care compositions, wherein the MLV comprises one or more ingredients selected from: polyglyceryl-10 dilinoleate, polyglyceryl-10 dipalmitate, polyglyceryl-10 dioleate, Caprylic/Capric Triglyceride, and combinations thereof.

1.27. Any of the preceding skin care compositions, wherein the skin care composition is delivered using a transdermal injection (e.g., mesotherapy).

1.28. Any of the preceding skin care compositions further comprising hyaluronic acid (HA). The amount of hyaluronic acid in the skin care composition may be from about 0.5 to about 5 wt. %, based on the total weight of the skin care composition. For example, the total amount of hyaluronic acid in the skin care composition may be from about 0.5 to about 5 wt. %, about 0.5 to about 4 wt. %, about 0.5 to about 3 wt. %, about 0.5 to about 2 wt. %, about 0.5 to about 1.5 wt. %, about 0.5 to about 1 wt. %; from about 0.75 to about 5 wt. %, about 0.75 to about 4 wt. %, about 0.75 to about 3 wt. %, about 0.75 to about 2 wt. %, about 0.75 to about 1.5 wt. %; from about 1 to about 5 wt. %, about 1 to about 4 wt. %, about 1 to about 3 wt. %, about 1 to about 2 wt. %, about 1 to about 1.5 wt. %; from about 1.5 to about 5 wt. %, about 1.5 to about 4 wt. %, about 1.5 to about 3 wt. %, about 1.5 to about 2 wt. %; from about 2 to about 5 wt. %, about 2 to about 4 wt. %, about 2 to about 3 wt. %; from about 3 to about 5 wt. %, about 3 to about 4 wt. %, or any range or subrange thereof, based on the total weight of the skin care composition 1.29. The preceding compositions, wherein the HA is low molecular weight HA (e.g., ≤avg 300 kDA).

1.30. The preceding composition, wherein the hyaluronic acid has a molecular weight (MW) of about 100,000 Da or less. In some embodiments, the molecular weight of the hyaluronic acid is from about 10 kDa to about 75 kDa, from about 25 kDa to 75 kDa, about 35 kDa to about 75 kDa, about 40 kDa to about 75 kDa, about 45 kDa to about 75 kDa, about 50 kDa to about 75 kDa, about 55 kDa to about 75 kDa, about 60 kDa to about 75 kDa; from about 10 kDa to about 65 kDa, about 25 kDa to 65 kDa, about 35 kDa to about 65 kDa, about 40 kDa to about 65 kDa, about 45 kDa to about 65 kDa, about 50 kDa to about 65 kDa, about 55 kDa to about 65 kDa; from about 10 kDa to about 60 kDa, about 25 kDa to 60 kDa, about 35 kDa to about 60 kDa, about 40 kDa to about 60 kDa, about 45 kDa to about 60 kDa, about 50 kDa to about 60 kDa; from about 10 kDa to about 55 kDa, about 25 kDa to 55 kDa, about 35 kDa to about 55 kDa, about 40 kDa to about 55 kDa, about 45 kDa to about 55 kDa; from about 10 kDa to about 50 kDa, about 25 kDa to 50 kDa, about 35 kDa to about 50 kDa, about 40 kDa to about 50 kDa; from about 10 kDa to about 45 kDa, about 25 kDa to 45 kDa; from about 10 kDa to about 40 kDa, about 25 kDa to 40 kDa, about 30 kDa to about 40 kDa, or any range or subrange thereof. In at least one embodiment, the skin care composition comprises hyaluronic acid having a molecular weight of about 50 kDa.

1.31. Any of the preceding skin care compositions comprising:
taurine, arginine, and glycine, wherein the skin care composition has a weight ratio of taurine to arginine to glycine (taurine:arginine:glycine) of (1.5-69):(0.5-40):(0.5-1.5), respectively (e.g., in a weight ratio of about (65):(34):(1), respectively);
ergothioneine (EGT);
alpha-tocopherol; and
Vitamin B3/niacinamide.

1.32. Any of the preceding skin care compositions comprising:
taurine, arginine and glycine, wherein the skin care composition has a weight ratio of taurine to arginine to glycine (taurine:arginine:glycine) of (1.5-69):(0.5-40):(0.5-1.5), respectively (e.g., in a weight ratio of about (65):(34):(1), respectively);
ergothioneine (EGT);
alpha-tocopherol; and
pyrrolidone carboxylic acid and/or a salt thereof (e.g., sodium PCA).

1.33. Any of the preceding skin care compositions comprising:
taurine, arginine and glycine, wherein the skin care composition has a weight ratio of taurine to arginine to glycine (taurine:arginine:glycine) of (1.5-69):(0.5-40):(0.5-1.5), respectively (e.g., in a weight ratio of about (65):(34):(1), respectively);
ergothioneine (EGT);
alpha-tocopherol;
pyrrolidone carboxylic acid and/or a salt thereof (e.g., sodium PCA); and
Vitamin B3/Niacinamide.

1.34. Any of the preceding skin care compositions comprising:
ergothioneine (EGT);
alpha-tocopherol; and
pyrrolidone carboxylic acid and/or a salt thereof (e.g., sodium PCA),
wherein the skin care composition has a weight ratio of alpha-tocopherol to EGT to pyrrolidone carboxylic acid and/or a salt thereof (alpha-tocopherol:EGT: pyrrolidone carboxylic acid and/or a salt thereof) of (0.5-2):(0.5-20):(0.5-20), respectively (e.g., 1:1:1) (e.g., 1:1:2) (e.g., 1:10:10), wherein the weight ratios are given with respect to the raw material weight % of the ingredients.

1.35. Any of the preceding compositions comprising:
ergothioneine (EGT);
alpha-tocopherol; and
niacinamide,
wherein the alpha-tocopherol:EGT:niacinamide are in a weight ratio of (0.5-2):(0.5-20):(0.5-20), respectively (e.g., 1:1:1) (e.g., 1:1:2) (e.g., 1:1:3) (e.g., 1:2:1) (e.g., 1:3:1) (e.g., 2:1:1) and (e.g., 3:1:1), wherein the weight ratios are given with respect to the raw material weight % of the ingredients.

1.36. Any of the preceding compositions comprising:
ergothioneine (EGT);
alpha-tocopherol; and
pyrrolidone carboxylic acid and/or a salt thereof (e.g., sodium PCA),
wherein the skin care composition has a weight ratio of alpha-tocopherol:EGT:pyrrolidone carboxylic acid and/or a salt thereof (alpha-tocopherol:EGT:pyrrolidone carboxylic acid and/or a salt thereof) of (50-250):(0.5-20):(50-250), respectively (e.g., 50:1:50, 50:1:100, 50:1:150, 50:1:200, 50:1:250, 100:1:50, 100:1:100, 100:1:150, 100:1:200, 100:1:250, 150:1:50, 150:1:100, 150:1:150, 150:1:200, 150:1:250, 200:1:50, 200:1:100, 200:1:150, 200:1:200, 200:1:250, 250:1:50, 250:1:100, 250:1:150, 250:1:200, 250:1:250, or any range or subrange thereof), wherein the weight ratios are based on the active material weight % of the ingredients.

1.37. Any of the preceding skin care compositions comprising:
ergothioneine (EGT);
alpha-tocopherol; and
niacinamide
wherein the skin care composition has a weight ratio of alpha-tocopherol to EGT to niacinamide (alpha-tocopherol:EGT:niacinamide) of (50-250):(0.5-20): (100-500), respectively (e.g., 50:1:100, 50:1:150, 50:1:200, 50:1:250, 50:1:300, 50:1:350, 50:1:400, 50:1:450, 50:1:500, 100:1:100, 100:1:150, 100:1:200, 100:1:250, 100:1:300, 100:1:350, 100:1:400, 100:1:450, 100:1:500, 150:1:100, 150:1:150, 150:1:200, 150:1:250, 150:1:300, 150:1:350, 150:1:400, 150:1:450, 150:1:500, 200:1:100, 200:1:150, 200:1:200, 200:1:250, 200:1:300, 200:1:350, 200:1:400, 200:1:450, 200:1:500, 250:1:100, 250:1:150, 250:1:200, 250:1:250, 250:1:300, 250:1:350, 250:1:400, 250:1:450, 250:1:500, or any range or subrange thereof), wherein the weight ratios are based on the active material weight % of the ingredients.

1.38. Any of the preceding skin care compositions comprising:
ergothioneine (EGT);
alpha-tocopherol;
niacinamide; and
pyrrolidone carboxylic acid and/or a salt thereof (e.g., sodium PCA).

1.39. The skin care composition of any of the preceding compositions comprising (wt. %):

| Ingredients | A* | B* | C** | D* |
|---|---|---|---|---|
| Ergothioneine (EGT) | 0.005 | 0.006 | 0.05 | 0.5 |
| Taurine | 1.300 | 1.62 | 0.65 | 1.300 |
| Arginine | 0.680 | 0.847 | 0.34 | 0.680 |
| Glycine | 0.02 | 0.025 | 0.01 | 0.02 |
| DL-alpha-tocopherol | 1.0 | 1.25 | 0.50 | 1.0 |
| Vitamin B3/Niacinamide | 2.0 | 2.5 | 1.01 | 2.0 |
| Sodium PCA | 1.0 | 1.25 | 2.01 | 1.0 |
| Hyaluronic Acid (e.g., MW of 50 kDa) | 1.0 | 0.50 | 0.25% | 0.25-1.0 |
| Additional Active Ingredients (e.g., carnosine, magnesium sulfate, nicotinamide adenine dinucleotide) | 1.02 | 1.27 | 0.26% | 1.02 |
| Multilamellar vesicle (MLV) | — | 49 | — | 49 |
| Water | — | q.s. (to balance) | — | q.s. (to balance) |
| Total | 100 | 100 | 100 | 100 |

*Columns A, B, and D: Amounts given in active weight % unless specified otherwise.
**Column C: Amounts given in raw material weight %.

1.40. Any of the preceding skin care compositions, wherein the skin care composition is delivered using a transdermal injection (e.g., mesotherapy).

1.41. Any of the preceding skin care compositions wherein one or more ingredients are encapsulated in a delivery vesicle (e.g., a multilamellar vesicle (MLV)).

1.42. Any of the preceding skin care compositions wherein one or more ingredients are encapsulated in a delivery vesicle (e.g., a multilamellar vesicle (MLV)), wherein between 0.1%-15% of the ingredients in the final formulation are encapsulated in the delivery vesicle (e.g., MLV) (e.g., about 10%).

1.43. The preceding composition wherein the delivery vesicle is an MLV and wherein the MLV encapsulates the following ingredients:
  i. niacinamide;
  ii. carnosine;
  iii. alpha-tocopherol; and
  iv. taurine, arginine and glycine 1.44. The preceding composition, wherein the weight ratio of taurine, arginine and glycine:niacinamide:carnosine:alpha-tocopherol is about 2:1:1:1 or 2:2:1:1, respectively.

1.45. Any of the preceding skin care compositions, wherein the skin care composition is in the form selected from: a serum, a cream, a moisturizer, a mask, a cleanser, oil, salve, lotion, gel, ointment, paste a facial make-up, and a balm (e.g., lip balm)

1.46. Any of the preceding compositions, wherein the composition comprises a thickener.

1.47. Any of the preceding compositions, wherein the thickener comprises a gum, optionally selected from xanthan gum, carrageenan, and a combination thereof.

1.48. Any of the preceding compositions, wherein the composition comprises a humectant, optionally wherein the humectant is selected from glycerin, sorbitol, and a combination thereof.

1.49. Any of the preceding compositions, comprising an additional antioxidant(s) selected from the group consisting of: flavonoids, phytoalexins, carnosine, ascorbic acid, tocotrienol, a lipoic acid, a carotenoid, melatonin, and any combinations thereof.

1.50. Any of the preceding compositions, further comprising an anti-inflammatory agent selected from the group consisting of: dexamethasone, prednisolone, corticosterone, budesonide, sulfasalazine, mesalamine, cetirizine, diphenylhydramine, antipyrine, methyl salicylate, loratadine, thymol, carvacrol, bisabolol, allantoin, eucalyptol, phenazone, propyphenazone, a nonsteroidal anti-inflammatory drug NSAID, and any combinations thereof.

1.51. Any of the preceding compositions further comprising an anti-itching agent, wherein the agent is selected from the group consisting of methyl sulphonyl methane, sodium bicarbonate, calamine, allantoin, kaolin, peppermint, tea tree oil, camphor, menthol, and hydrocortisone, and any combinations thereof.

1.52. Any of the preceding skin care compositions, wherein the skin care composition is formulated to have a weight ratio of alpha-tocopherol to EGT of about 6:1 to about 1:6. Preferably, the skin care composition has a weight ratio of alpha-tocopherol to EGT from about 6:1 to about 1:6, about 5:1 to about 1:6, about 4:1 to about 1:6, about 3:1 to about 1:6, about 2:1 to about 1:6, about 1:1 to about 1:6; from about 6:1 to about 1:5, about 5:1 to about 1:5, about 4:1 to about 1:5, about 3:1 to about 1:5, about 2:1 to about 1:5, about 1:1 to about 1:5; from about 6:1 to about 1:4, about 5:1 to about 1:4, about 4:1 to about 1:4, about 3:1 to about 1:4, about 2:1 to about 1:4, about 1:1 to about 1:4; from about 6:1 to about 1:3, about 5:1 to about 1:3, about 4:1 to about 1:3, about 3:1 to about 1:3, about 2:1 to about 1:3, about 1:1 to about 1:3; from about 6:1 to about 1:2, about 5:1 to about 1:2, about 4:1 to about 1:2, about 3:1 to about 1:2, about 2:1 to about 1:2, about 1:1 to about 1:2; from about 6:1 to about 1:1, about 5:1 to about 1:1, about 4:1 to about 1:1, about 3:1 to about 1:1, about 2:1 to about 1:1, about 1:1, or any range or subrange thereof.

1.53. Additionally or alternatively, the skin care compositions may be formulated to have a weight ratio of alpha-tocopherol to niacinamide and/or EGT to niacinamide of about 1:1 to about 1:11. In some embodiments, the skin care compositions has a weight ratio of alpha-tocopherol to niacinamide and/or EGT to niacinamide from about 1:1 to about 1:11, about 1:1 to about 1:9, about 1:1 to about 1:7, about 1:1 to about 1:6, about 1:1 to about 1:5, about 1:1 to about 1:4, about 1:1 to about 1:3; from about 1:2 to about 1:11, about 1:2 to about 1:9, about 1:2 to about 1:7, about 1:2 to about 1:6, about 1:2 to about 1:5, about 1:2 to about 1:4, about 1:2 to about 1:3; from about 1:3 to about 1:11, about 1:3 to about 1:9, about 1:3 to about 1:7, about 1:3 to about 1:6, about 1:3 to about 1:5, about 1:3 to about 1:4, about 1:3, or any range or subrange thereof.

1.54. Additionally or alternatively, the skin care compositions may be formulated to have a weight ratio of alpha-tocopherol to pyrrolidone carboxylic acid and/or a salt thereof and/or EGT to pyrrolidone carboxylic acid and/or a salt thereof of about 1:1 to about 1:11. In some embodiments, the skin care compositions has a weight ratio of alpha-tocopherol to pyrrolidone carboxylic acid and/or a salt thereof and/or EGT to pyrrolidone carboxylic acid and/or a salt thereof from about 1:1 to about 1:11, about 1:1 to about 1:9, about 1:1 to about 1:7, about 1:1 to about 1:6, about 1:1 to about 1:5, about 1:1 to about 1:4, about 1:1 to about 1:3; from about 1:2 to about 1:11, about 1:2 to about 1:9, about 1:2 to about 1:7, about 1:2 to about 1:6, about 1:2 to about 1:5, about 1:2 to about 1:4, about 1:2 to about 1:3; from about 1:3 to about 1:11, about 1:3 to about 1:9, about 1:3 to about 1:7, about 1:3 to about 1:6, about 1:3 to about 1:5, about 1:3 to about 1:4, about 1:3, or any range or subrange thereof.

1.55. Any of the preceding skin care compositions, wherein the skin care composition comprises a weight ratio of alpha-tocopherol to EGT to pyrrolidone carboxylic acid and/or a salt thereof (alpha-tocopherol:EGT:pyrrolidone carboxylic acid and/or a salt thereof) of (0.5-2):(0.5-20):(1-20), respectively (e.g., 1:1:1) (e.g., 1:1:2) (e.g., 1:10:10), where the weight ratios are based upon the weights of the ingredients relative to the total weight of the composition.

1.56. Any of the preceding compositions, wherein the skin care composition comprises alpha-tocopherol:EGT:sodium PCA in a weight ratio of (50-250):(0.5-20):(50-250), respectively (e.g., (200:1:200), where the weight ratios are based on the active material weight % of the ingredients relative to the total weight of the composition. In certain embodiments, the skin care composition may be formulated to have a weight ratio of alpha-tocopherol to EGT to pyrrolidone carboxylic acid and/or a salt thereof (alpha-tocopherol:EGT:pyrrolidone carboxylic acid and/or a salt thereof) from about 1:2:6 to about 1:0.5:1.5, from about 1:1.5:4 to about 1:0.75:2; about 1:1.1:3.3 to about 1:0.9:2.7.

1.57. Any of the preceding skin care compositions, wherein the skin care composition comprises a weight ratio of alpha-tocopherol to EGT to niacinamide (alpha-tocopherol:EGT:niacinamide) in a weight ratio of (0.5-2):(1-20):(1-20), respectively (e.g., 1:1:1) (e.g., 1:1:2) (e.g., 1:1:3), where the weight ratios are based upon the raw material weight % of the ingredients relative to the total weight of the composition. In certain embodiments, the skin care composition may be formulated to have a weight ratio of alpha-tocopherol to EGT to niacinamide (alpha-tocopherol:EGT:niacinamide) from about 1:2:6 to about 1:0.5:1.5, from about 1:1.5:4 to about 1:0.75:2; about 1:1.1:3.3 to about 1:0.9:2.7.

1.58. Any of the preceding compositions, wherein the skin care composition comprises a weight ratio of alpha-tocopherol to EGT to niacinamide (alpha-tocopherol:EGT:niacinamide) in a weight ratio of (100-250):(0.5-5):(200-600) (e.g., 200:1:400), where the weight ratios are based on the active material weight % of the ingredients.

1.59. Any of the preceding skin care compositions, wherein the skin care composition comprises:
niacinamide (e.g., from 0.5%-5% by wt. of the composition) (e.g., about 3% by wt.);
alpha-tocopherol (e.g., from 0.1%-2% by wt. of the composition) (e.g., about 0.5% by wt.); and
ergothioneine (EGT) (e.g., from 0.001-0.005% by wt. of the composition) (e.g., about 0.0025% by wt.).

1.60. The preceding skin care composition, wherein the skin care composition further comprises:
ascorbyl glucoside (e.g., from 0.5%-5% by wt. of the composition) (e.g., about 2% by wt.), wherein the ascorbyl glucoside is present in an amount preferably from about 1 to about 5 wt. %, about 1 to about 4 wt. %, about 1 to about 3 wt. %, about 1 to about 2 wt. %; from about 2 to about 5 wt. %, about 2 to about 4 wt. %, about 2 to about 3 wt. %; about 3 to about 5 wt. %, about 3 to about 4 wt. %, or any range or subrange thereof, based on the total weight of the skin care composition; and
astaxanthin (e.g., from 0.001%-0.05% by wt. of the composition) (e.g., about 0.01% by wt.).

1.61. Any of the preceding skin care compositions, wherein the skin care composition comprises:
ergothioneine (EGT);
alpha-tocopherol;
niacinamide (vitamin B);
pyrrolidone carboxylic acid and/or a salt thereof (e.g., sodium PCA);
hyaluronic acid (e.g., having a MW of 50 kDa);
magnesium sulfate; and
nicotinamide adenine dinucleotide (NAD).

The present disclosure provides, in another aspect, a personal care composition (Composition 2.0), e.g., skin care composition for use in inhibiting, treating or reducing damage to the skin caused reactive oxygen species. In one aspect, the skin care composition for use can be any of Composition 1.0 et seq.

The present disclosure provides, in another aspect, a method of inhibiting, treating or reducing damage to the skin caused reactive oxygen (Method 1.0), wherein the method comprises administering to a subject in need thereof an effective amount of any of Composition 1.0 et seq.

1.1 Method 1.0, where the skin care composition (e.g., any of Composition 1.0 et seq) is delivered via a transdermal injection.
1.2 Method 1.0, wherein the skin care composition is topically delivered to the skin using a serum, a cream, a moisturizer, a mask, a cleanser, oil, salve, lotion, gel, ointment, paste a facial make-up a toner, an essence and a balm (e.g., lip balm).

In another aspect, the present disclosure provides a method of depositing a topically active compound on the skin (Method 2.0), comprising applying an effective amount of any of skin care compositions disclosed herein, e.g., any of Compositions 1 et seq., to the skin.

2.1 Method 2.0, where the skin care composition (e.g., any of Composition 1.0 et seq) is delivered via a transdermal injection.
2.2 Method 2.0, wherein the skin care composition is topically delivered to the skin using a serum, a cream, a moisturizer, a mask, a cleanser, oil, salve, lotion, gel, ointment, paste a facial make-up, a toner, an essence and a balm (e.g., lip balm).

In another aspect, the present disclosure provides a method selected from the following (Method 3.0):
vitalization of skin cells in a subject in need thereof;
enhancing cellular energy in skin cells (e.g., dermal cells) in a subject in need thereof;
reduction or inhibition of cellular damage (e.g., from reactive oxygen species, UV light damage) in a subject in need thereof; and
cellular detoxification (e.g., in dermal cells) in a subject in need thereof,
wherein any of the above methods comprises applying an effective amount of any of skin care compositions disclosed herein, e.g., any of Compositions 1 et seq., to the skin.

3.1 Method 3.0, where the skin care composition (e.g., any of Composition 1.0 et seq) is delivered via a transdermal injection.
3.2 Method 3.0, wherein the skin care composition is topically delivered to the skin using a serum, a cream, a moisturizer, a mask, a cleanser, oil, salve, lotion, gel, ointment, paste a facial make-up, a toner, an essence and a balm (e.g., lip balm).

In another aspect, the present disclosure provides a method selected from the following (Method 4.0):
- treatment of redness and/or reduction skin pore size in a subject in need thereof;
- treatment of fine lines, wrinkles, or scars in a subject in need thereof;
- treatment to increase smoothness, hydration, and/or elasticity of the skin in a subject in need thereof;
- reduction or inhibition of cellular damage (e.g., from reactive oxygen species, UV light damage) in a subject in need thereof; and
- Cellular detoxification (e.g., in dermal cells) in a subject in need thereof, wherein any of the above methods comprises applying an effective amount of any of skin care compositions disclosed herein, e.g., any of Compositions 1 et seq., to the skin.

4.1 Method 4.0, where the skin care composition (e.g., any of Composition 1.0 et seq) is delivered via a transdermal injection.

4.2 Method 4.0, wherein the skin care composition is topically delivered to the skin using a serum, a cream, a moisturizer, a mask, a cleanser, oil, salve, lotion, gel, ointment, paste a facial make-up, a toner, an essence and a balm (e.g., lip balm).

In some embodiments, the skin care composition, e.g., any of Composition 1.0 et seq., comprises an oil selected from sunflower seed oil, olive oil, shear butter, jojoba oil, almond oil, grape seed oil, rose hip seed oil, mink oil, castor oil, soybean oil, mineral oil, and a combination thereof, optionally wherein the oil is sunflower seed oil.

In some embodiments, the skin care composition, e.g., any of Composition 1.0 et seq., comprises a thickener. In some embodiments, the thickener comprises a gum, optionally selected from xanthan gum, carrageenan and a combination thereof.

In some embodiments, the skin care composition e.g., any of Composition 1.0 et seq., comprises a humectant, optionally wherein the humectant is selected from glycerin, sorbitol, and a combination thereof.

In some embodiments, the skin care composition, e.g., any of Composition 1.0 et seq., comprises water.

In some embodiments, the skin care composition, e.g., any of Composition 1.0 et seq., is free or substantially free of sulfate.

In some embodiments, the skin care composition, e.g., any of Composition 1.0 et seq., further comprises, a gelling agent, an additional antioxidant, a fragrance, or a combination thereof.

In some embodiments, the composition, e.g., any of Composition 1.0 et seq., is in the form selected from: a serum, a cream, a moisturizer, a mask, a cleanser, a facial make-up, and a balm (e.g., lip balm).

The composition of the present disclosure, e.g., any of Composition 1.0 et seq., may be any type of personal care composition. In certain embodiments, the composition is any composition that can be formulated into topical skin care formulations suitable for application to skin. Examples of such compositions include, but are not limited to: serums, creams, moisturizers, masks, cleanser (e.g., facial cleansers), a facial make-up, balms (e.g., lip balm), and cosmetics. The composition can comprise a single phase or can be a multi-phase system, for example a system comprising a polar phase and an oil phase, optionally in the form of a stable emulsion. In certain aspects, skin care compositions of the disclosure are formulated in a manner suitable for topically injection.

The compositions of the disclosure (e.g., any of Composition 1.0 et seq) can be liquid, semi-solid or solid. The formulation can be provided in any suitable container, tube, or container with a porous cap, roll-on container, bottle, container with an open end, etc.

In some aspects, water may be present in the skin care compositions of the disclosure, e.g., any of Composition 1.0 et seq. Water employed in the preparation of commercial personal care compositions should be deionized and free of organic impurities. When it is incorporated into the formulation, water can make up the balance of the compositions and includes about 10% to about 90%, or about 10% to about 80%, by weight of the skin care compositions. This amount of water includes the free water which is added plus that amount which is introduced with other materials such as glycerin, sorbitol or any components of the disclosure.

In some embodiments, the skin care compositions of the disclosure, e.g., any of Composition 1.0 et seq., can include one or more pH adjusters. When incorporated in the formulation, the pH adjuster can include, but is not limited to, lactic acid, sodium hydroxide, and/or citric acid.

In some embodiments, the skin care compositions, e.g., any of Composition 1.0 et seq., may further comprise a betaine zwitterionic surfactant. In some aspects, the betaine zwitterionic surfactant may be a $C_8$-$C_{16}$ aminopropyl betaine, e.g., cocamidopropyl betaine.

In some embodiments, the skin care compositions described herein, e.g., any of Composition 1.0 et seq., may further comprises a non-ionic block copolymer is selected from: Poloxamer 338, Poloxamer 407, Poloxamer, 237, Poloxamer, 217, Poloxamer 124, Poloxamer 184, Poloxamer 185, and a combination of two or more thereof.

As used herein, the term "effective amount" means the quantity of an active ingredient and/or skin care composition required to provide adequate protection against damage caused or related to reactive oxygen species.

As used herein, "substantially free" of a material may refer to a composition where the material is present in an amount of less than 0.1 weight %, less than 0.05 weight %, less than 0.01 weight %, less than 0.005 weight %, less than 0.001 weight %, or less than 0.0001 weight % based on a total weight of the composition.

As used herein, "skin care composition" is meant to refer to a composition for which the intended use can include promotion or improvement of health, cleanliness, odor, appearance, and/or attractiveness of skin. For example, skin care compositions can be in the form of a serum, a cream, a moisturizer, a mask, a cleanser, oil, salve, lotion, gel, ointment, paste, a facial make-up, a toner, an essence, and a balm (e.g., lip balm). Skin care compositions of the disclosure, e.g., any of Composition 1.0 et seq., can be applied topically to the skin by a user or consumer. In some aspects, skin care compositions of the disclosure can be applied by injection (e.g., subcutaneous or dermal injection). In certain aspects, skin care composition is intended to refer to a product for use at home or in a professional setting.

In certain aspects, the skin care compositions of the disclosure (e.g., any of Composition 1.0 et seq) can comprises one or more topically active compounds selected from: antibacterial agents, vitamins, medicaments, fragrance materials, antioxidants and other skin-care ingredients.

As used herein, unless otherwise specified, "Vitamin E" refers to a family of four isomers of tocopherols and four isomers of tocotrienols. All eight isomers of vitamin E have a 6-chromanol ring structure and a side chain. The four tocopherols include fully saturated side chains and include alpha-tocopherol, gamma-tocopherol, beta-tocopherol, and delta-tocopherol. The four tocotrienols include unsaturated side chains and include alpha-tocotrienol, gamma-tocotrienol, beta-tocotrienol, and delta-tocotrienol. As used herein, unless otherwise specified, the term "vitamin E" may refer to any one or more of the eight isomers. For example, as used herein, vitamin E may be or include one or more of alpha-tocopherol, gamma-tocopherol, beta-tocopherol, delta-tocopherol, alpha-tocotrienol, gamma-tocotrienol, beta-tocotrienol, delta-tocotrienol, or any combination thereof. In at least one implementation, the vitamin E includes at least one of the four tocopherols. It should be appreciated that the vitamin E and/or the isomers thereof may be or include natural forms of vitamin E, synthetic forms of vitamin E, or combinations thereof. Any one or more of the isomers of vitamin E may be in the "d" form, the "l" form, or combinations thereof. In some embodiments, vitamin E is vitamin E acetate or Vitamin E succinate. In some embodiments, vitamin E is vitamin E acetate.

As used herein, "Vitamin C" may be ascorbic acid or derivatives thereof. Ascorbic acid exists as two enantiomers commonly denoted "l" (for "levo") and "d" (for "dextro"). The "l" isomer is the one most often encountered. Ascorbic acid is also referred to as L(+)-ascorbic acid or l-ascorbic acid. The ascorbic acid derivatives may be or include, but are not limited to, L-ascorbic acid, calcium ascorbate, calcium l-ascorbate dihydrate, magnesium ascorbate, potassium ascorbate, magnesium L-ascorbyl phosphate (also referred to as: magnesium ascorbate phosphate or ascorbic acid phosphate magnesium salt), L-ascorbic acid 2-phosphate sesquimagnesium salt hydrate, (+) sodium L-ascorbate, dehydro-1-(+)-ascorbic acid dimer, sodium ascorbyl phosphate (also referred to as: ascorbic acid phosphate sodium salt, sodium 1-ascorbyl phosphate, 2-phospho-L-ascorbic acid trisodium salt, L-ascorbic acid 2-phosphate trisodium salt or sodium L-ascorbyl-2-phosphate), ascorbic acid-2-glucoside, ascorbyl dipalmitate, ascorbyl methylsilanol pectinate, ascorbyl stearate, disodium ascorbyl sulfate, ascorbyl 6-palmitate, calcium ascorbyl phosphate, ascorbyl acetate, ascorbyl propionate, ascorbyl stearate, ascorbyl palmitate, ascorbyl dipalmitate, ascorbyl glucoside, ascorbic acid polypeptide, ethyl ascorbyl ether, ascorbyl ethyl silanol pectinate, or the like, or combinations thereof.

As used herein, "vitamin D" refers to a group of fat-soluble secosteroids responsible for increasing intestinal absorption of calcium, magnesium, and phosphate, and many other biological effects. The two major forms are vitamin $D_2$ or ergocalciferol, and vitamin $D_3$ or cholecalciferol. Vitamin D includes vitamin D (mixture of molecular compounds of ergocalciferol with lumisterol), vitamin $D_2$ (ergocalciferol), vitamin $D_3$ (cholecalciferol), vitamin $D_4$ (22-dihydroergocalciferol), and vitamin $D_5$ (sitocalciferol).

As used herein, "vitamin K" is a group of compounds with a common chemical structure of 2-methyl-1,4-naphthoquinone. Vitamin K plays a role in blood clotting, bone metabolism, and regulating blood calcium levels. Vitamin K includes vitamin $K_1$ (phylloquinone) and vitamin $K_2$ (menaquinone). Vitamin $K_2$ have unsaturated isoprenyl side chains and are designated as MK-4 through MK-13, based on the length of their side chain.

Optional ingredients that may be included in the skin care composition of the invention include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments.

The skin care compositions of the disclosure, e.g., any of Composition 1.0 et seq., may optionally contain emollients in any desired amount to achieve a desired emollient effect. Emollients are known in the art and are used to impart a soothing effect on the skin. Non-volatile emollients are preferable. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material is phenyl trimethicone. Examples include, but are not limited to, PPG-14 butyl ether, PPG-3 myristyl ether, secondary alcohol ethoxylates, stearyl alcohol, stearic acid and salts thereof, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl)adipate), Di-(2-ethyl hexyl)succinate, isopropyl myristate, isopropyl palmitate, isopropyl stearate, octacosanol, butyl stearate, glyceryl monostearate, polyethylene glycols, oleic acid, triethylene glycol, lanolin, castor oil, sunflower seed oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide. In some embodiments, the composition comprises an oil selected from sunflower seed oil, olive oil, shear butter, jojoba oil, almond oil, grape seed oil, rose hip seed oil, mink oil, castor oil, soybean oil, mineral oil, and a combination thereof. In certain embodiment, the composition comprises sunflower seed oil.

The skin care compositions of the disclosure, e.g., any of Composition 1.0 et seq., may optionally include one or more humectants. Humectants can reduce evaporation and also contribute towards preservation by lowering water activity and can also impart desirable sweetness or flavor to compositions. Illustrative humectants may be or include, but are not limited to, glycerin, propylene glycol, polyethylene glycol, sorbitol, xylitol, or the like, or any mixture or combination thereof. In some embodiment, the humectant is selected from glycerin, sorbitol and a combination thereof. In certain embodiment, the humectant is glycerin.

The skin care compositions of the disclosure, e.g., any of Composition 1.0 et seq., may optionally include thickeners. Illustrative thickeners may be or include, but are not limited to, colloidal silica, fumed silica, a cross-linked polyvinylpyrrolidone (PVP) polymer, cross-linked polyvinylpyrrolidone (PVP), or the like, or mixtures or combinations thereof. In some embodiments, the thickening system includes a cross-linked polyvinylpyrrolidone (PVP) polymer. Illustrative thickeners may also be or include, but are not limited to, carbomers (e.g., carboxyvinyl polymers), carrageenans (e.g., Irish moss, carrageenan, iota-carrageenan, etc.), high molecular weight polyethylene glycols, cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, or the like, or mixtures or combinations thereof. In some embodiments, the thickener comprises or is a gum, optionally selected from xanthan gum, carrageenan, and a combination thereof.

The skin care compositions of the disclosure, e.g., any of Composition 1.0 et seq., may optionally include one or more gelling agents. Examples of gelling agents include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, or other cosmetically acceptable materials, which are solid or semi-solid at room temperature and provide a consistency suitable for application to the skin.

The skin care compositions of the disclosure, e.g., any of Composition 1.0 et seq., may optionally one or more antioxidants. For example, one or more antioxidants may be added to the composition to act as ingredient protectants and for maintenance of long-term stability of the composition. Examples of optional antioxidants include, but are not limited to citric acid, butylated hydroxytoluene, pentaerythrityl tetra-di-t-butyl hydroxyhydrocinnamate.

The skin care compositions of the disclosure, e.g., any of Composition 1.0 et seq., may optionally polymeric materials for thickening, such as polyamides, cellulose derivatives (e.g., hydroxypropylcellulose, hydroxypropyl methyl cellulose, etc.) and natural or synthetic gums, such as polyglycerides including agar, agarose, pectin, or guars or mixtures or combinations thereof. One class of materials worthy of attention for thickening a water-immiscible phase comprises derivatives of hydrolysed starch or other polysaccharides, including in particular esterified dextrins, such as dextrin palmitate. A further class of polymers that is particularly directed to structuring an oil phase containing a silicone oil comprises polysiloxane elastomers. Suspending agents such as silicas or clays such as bentonite, montmorillonite or hectorite, including those available under the trademark Bentone can also be employed to thicken liquid compositions according to the invention. The composition can be thickened with non-polymeric organic gellants, including selected dibenzylidene alditols (e.g., dibenzylidene sorbitol).

The skin care compositions of the disclosure, e.g., any of Composition 1.0 et seq., may optionally include a fragrance. Any fragrance suitable for skin care use may be incorporated into the skin care composition of the disclosure. Fragrances tend to be relatively volatile aroma compounds which are capable of entering the gas phase at skin surface temperature.

The skin care compositions of the disclosure, e.g., any of Composition 1.0 et seq., may be manufactured using methods known in the art. Typically, the ingredients are combined and optionally heated where components need to be melted. The components are mixed. Desirably, volatile materials such as fragrant materials are incorporated in the composition in the latter stages of a mixing cycle in order to avoid volatilization thereof. After mixing, the composition may be poured directly into the dispensers and the container capped to preserve the product until use.

EXAMPLES

Example 1

Non-limiting, example skin care compositions (Example Compositions A-D) were prepared according to aspects of the disclosure. The formulations of Example Compositions A-D are provided in Table 1, below (wt. % of active material unless indicated otherwise):

TABLE 1

| Ingredient | A* | B* | C** | D* |
|---|---|---|---|---|
| Ergothioneine (EGT) | 0.005% | 0.006% | 0.05% | 0.5% |
| Taurine | 1.300 | 1.62 | 0.65 | 1.300 |
| Arginine | 0.680 | 0.847 | 0.34 | 0.680 |
| Glycine | 0.02 | 0.025 | 0.01 | 0.02 |
| DL-alpha-tocopherol | 1.0 | 1.25 | 0.50 | 1.0 |
| Vitamin B3/Niacinamide | 2.0 | 2.5 | 1.01 | 2.0 |
| Sodium PCA | 1.0 | 1.25 | 2.01 | 1.0 |
| Hyaluronic Acid (e.g., 50 kDa) | 1.0 | 0.50 | 0.25% | 0.25-1.0 |
| Additional Active Ingredients (e.g., carnosine, magnesium sulfate, nicotinamide adenine dinucleotide) | 1.02 | 1.27 | 0.26% | 1.02 |
| Multilamellar vesicle (MLV) | — | 49 | — | 49 |
| Water | — | q.s. (to balance) | — | q.s. (to balance) |
| Total | 100 | 100 | 100 | 100 |

*Columns A, B, and D: Amounts given in active weight % unless specified otherwise.
**Column C: Amounts given in raw material weight %.

Example 2—Combinations with Alpha-Tocopherol, Ergothioneine and Sodium PCA

In-vitro studies were conducted in a human derived keratinocyte cell culture model. Keratinocytes were treated with exogenous 0.3 wt. % hydrogen peroxide to induce reactive oxygen species (ROS) production. Hydrogen peroxide treated cells were subsequently treated with: alpha-tocopherol, Ergothioneine and Sodium PCA, respectively and in combination. Changes in ROS production were assessed using a ROS Detection Assay Kit and fluorescence microplate reader.

Sample Preparation: Human Derived Keratinocytes, Plated on 24-Well Plates

Raw Materials:
alpha-tocopherol
Ergothioneine
Sodium PCA
30% $H_2O_2$ (hydrogen peroxide)
Cellular ROS/Superoxide Detection Assay Kit (Abcam—ab139476)

Reagents:
Medium EpiLife (Life Technologies)
Human keratinocyte Growth Supplements (Life Technologies)

Stock Solutions:
1 wt. % alpha-tocopherol, was prepared by dissolving 10 uL of alpha-tocopherol (100%) in 990 uL of DMSO (100%).
0.1 wt. % alpha-tocopherol, was prepared by dissolving 100 uL of alpha-tocopherol (100%) in 900 uL of DMSO (100%).

1 wt. % Ergothioneine (EGT) was prepared by dissolving 10 uL of EGT in 990 uL respectively in deionized water.

10 wt. % Sodium PCA (NaPCA) was prepared by dissolving 1 mL of Na PCA (50%) in 5 mL of deionized water.

1 wt. % Sodium PCA (NaPCA) was prepared by dissolving 1 mL of Na PCA (50%) in 9 mL of deionized water.

3 wt. % $H_2O_2$ was prepared by dissolving 100 uL of $H_2O_2$ (30%) in 900 uL of deionized water.

10 wt. % of DMSO, was prepared by dissolving 100 uL DMSO (stock 100%)+900 uL cell culture media.

Dilutions:

alpha tocopherol: 1 wt. % stock in DMSO, filter-sterilized
Dilute 20 uL of (0.1%)+980 uL=1000 uL/1 mL of (0.001%) (2×)
Dilute 30 uL of (1%)+970 uL=1000 uL/mL of (0.001%) (3×)
Dilute 40 uL of (1%)+960 uL=1000 uL, of (0.001%) (4×)
Ergothioneine: 1 wt. % stock in dH2O, filter-sterilized
Dilute 20 uL of (1%)+980 uL=1000 uL/1 mL of (0.01%) (2×)
Dilute 30 uL of (1%)+970 uL=1000 uL/mL of (0.01%) (3×)
Dilute 40 uL of (1%)+960 uL=1000 uL, of (0.01%) (4×)
Sodium PCA: 1 wt. % stock in dH2O, filter-sterilized
Dilute 20 uL of (1%)+980 uL=1000 uL/1 mL of (0.01%) (2×)
Dilute 30 uL of (1%)+970 uL=1000 uL/mL of (0.01%) (3×)
Dilute 40 uL of (1%)+960 uL=1000 uL, of (0.01%) (4×)
$H_2O_2$: 3 wt. % stock in dH2O, filter-sterilized
Dilute 200 uL of (3%)+800 uL=1000 uL/1 mL of (0.3%) (2×)
Dilute 300 uL of (3%)+700 uL=1000 uL/mL of (0.01%) (3×)
Dilute 400 uL of (3%)+600 uL=1000 uL, of (0.01%) (4×)
DMSO: 10 wt. % stock in cell culture media
Dilute 10 uL (10% stock)+990 uL of cell culture media=1000 uL/1 mL of (0.1%) (1×)
Dilute 20 uL (10% stock)+980 uL of media=1000 uL/1 mL (2×)

TABLE 2

| | Types of treatment | Dilution | uls/well |
|---|---|---|---|
| A | DMSO | 1X | 500 uL |
| B | α- tocopherol(0.001%) | 2X | 250 uL |
| C | Ergothioneine (EGT) (0.01%) | 2X | 250 uL |
| D | Sodium PCA (Na PCA) (0.01%) | 2X | 250 uL |
| E | α- tocopherol (0.001%) + EGT(0.01%) + Na PCA(0.01%) | 3X | 167 uL each |
| F | DMSO + $H_2O_2$ (0.3%) | 2X | 250 uL + 250 uL |
| G | α- tocopherol(0.001%) + $H_2O_2$ (0.3%) | 2X | 250 uL + 250 uL |
| H | EGT (0.01%) + $H_2O_2$ (0.3%) | 2X | 250 ul + 250 uL |
| I | Na PCA (0.01%) + $H_2O_2$ (0.3%) | 2X | 250 uL + 250 uL |
| J | α- tocopherol (0.001%) + EGT(0.01%) + Na PCA(0.01%) + $H_2O_2$ (0.3%) | 4X | 125 uL each |

Cell Culture Treatment 500 uL of each treatment sample was directly applied to the 24-well plates and incubated for 30 mins.

Post incubation: each well was washed with the wash buffer (1×) provided.

250 uL of green Fluorescent (GF) dye containing media (2.5 uL of GF dye/250 uL of media) was then added to each well and incubate for 60 mins.

Post incubation, Fluorescence was read on a microplate reader at 490/525.

Test Products:

Test samples are listed in Table 3.

TABLE 3

| | Test Product | $H_2O_2$ (0.3%) | Description |
|---|---|---|---|
| A | DMSO | + | 0.1% of DMSO |
| F | DMSO | + | 0.1% of DMSO + 0.3% $H_2O_2$ in untreated media |
| G | Alpha-tocopherol (0.001%) | + | Alpha-tocopherol (0.001%) + 0.3% $H_2O_2$ in untreated media |
| H | EGT (0.01%) | + | EGT (0.01%) + 0.3% $H_2O_2$ in untreated media |
| I | Na PCA (0.01%) | + | Na PCA (0.01%) + 0.3% $H_2O_2$ in untreated media |
| J | Alpha-tocopherol (0.001%) + EGT (0.01%) + Na PCA (0.01%) | + | Alpha-tocopherol (0.001%) + EGT (0.01%) + Na PCA (0.01%) + 0.3% $H_2O_2$ in untreated media |

Results:

0.3 wt. % $H_2O_2$ treatment results in a significant increase in ROS produced by the human derived keratinocytes.

0.001 wt. % of α-tocopherol+0.01 wt. % EGT+0.01% Sodium PCA collective treatment in human derived keratinocyte culture resulted in a greater than 82% decrease in ROS generated (relative to the 0.3 wt. % of $H_2O_2$ treatment).

This decrease in ROS with a combinatorial treatment of α-tocopherol, EGT and sodium PCA is unexpected and significantly greater than the decrease observed by individual treatment by 0.001 wt. % of any of: α-tocopherol (70.72% decrease), 0.01 wt. % EGT (74.5% decrease) and 0.01 wt. % Sodium PCA (37.9%), individually.

Experiments were performed in three replicas. The results are shown in Tables 4 and 5 below.

TABLE 4

Significant Decrease in ROS generated in keratinocyte by antioxidant treatment (Fold Change (relative to untreated))

| | Treatment | P Values | Fold Change |
|---|---|---|---|
| A vs F | DMSO vs. 0.1 wt.% of DMSO + 0.3 wt.% $H_2O_2$ in untreated media | *** p < 0.0001 | 5.95-fold increase |
| F vs G | 0.1 wt. % of DMSO + 0.3 wt. % $H_2O_2$ in untreated media vs. Alpha-tocopherol (0.001%) | *** p < 0.0001 | 4.21-fold decrease |
| F vs H | 0.1 wt. % of DMSO + 0.3 wt. % $H_2O_2$ in untreated media vs. EGT (0.01%) | *** p < 0.0001 | 4.43-fold decrease |
| F vs I | 0.1 wt. % of DMSO + 0.3 wt. % $H_2O_2$ in untreated media vs. Na PCA (0.01%) | *** p < 0.0001 | 2.25-fold decrease |
| F vs J | 0.1 wt. % of DMSO + 0.3 wt. % $H_2O_2$ in untreated media vs. | *** p < 0.0001 | 4.92-fold decrease |

TABLE 4-continued

Significant Decrease in ROS generated in keratinocyte by antioxidant treatment (Fold Change (relative to untreated))

| Treatment | P Values | Fold Change |
|---|---|---|
| Alpha-tocopherol (0.001%) + EGT (0.01%) + Na PCA (0.01%) | | |

TABLE 5

Decrease in ROS generated in keratinocyte by antioxidant treatment (relative to untreated)

| | Treatment | $H_2O_2$ (0.3%) | % Decrease |
|---|---|---|---|
| A | DMSO | − | 87.77% |
| F | DMSO vs. 0.1 wt. % of DMSO + 0.3 wt. % $H_2O_2$ in untreated media | + | 0% |
| G | Alpha-tocopherol (0.001%) | + | 70.72% |
| H | EGT (0.01%) | + | 74.5% |
| I | Na PCA (0.01%) | + | 37.88% |
| J | Alpha-tocopherol (0.001%) + EGT (0.01%) + Na PCA (0.01%) | + | 82.78% |

The results demonstrate that a combination of α-tocopherol, Ergothioneine (EGT) and Sodium PCA exhibit a significant decrease in ROS production in human derived keratinocyte cell culture. This combination shows an unexpected impact in decreasing ROS production in keratinocytes (treated with 0.3% hydrogen peroxide) relative to each treatment alone.

Example 3—Combinations with Alpha-Tocopherol, Ergothioneine and Niacinamide

In-vitro studies were conducted in a human derived keratinocyte cell culture model. Keratinocytes were treated with exogenous 0.3 wt. % hydrogen peroxide to induce ROS production. Hydrogen peroxide treated cells were then treated with: alpha-tocopherol, ergothioneine and niacinamide, respectively and in combination. Changes in ROS production were then assessed using a ROS Detection Assay Kit and fluorescence microplate reader.

Sample Preparation: Human Derived Keratinocytes, Plated on 24-Well Plates
  Raw Materials:
  alpha-tocopherol
  Ergothioneine
  Niacinamide
  30% $H_2O_2$ (hydrogen peroxide)
  Cellular ROS/Superoxide Detection Assay Kit (Abcam—ab139476)
  Reagents:
  Medium EpiLife (Life Technologies)
  Human keratinocyte Growth Supplements (Life Technologies)
  Stock Solutions:
  1 wt. % alpha-tocopherol, is prepared by dissolving 10 uL of alpha-tocopherol (100%) in 990 uL of DMSO (100%).
  1 wt. % Ergothioneine (EGT) and Niacinamide are prepared by dissolving 10 mg/ml, followed by filter sterilization.
  3 wt. % $H_2O_2$ is prepared by dissolving 100 uL of $H_2O_2$ (30%) in 900 uL of deionized water.
  10% of DMSO, is prepared by dissolving 100 uL DMSO (stock 100%)+900 uL cell culture media.
  Dilutions:
  alpha tocopherol: 1 wt. % stock in DMSO, filter-sterilized
  Dilute 10 uL of (1%)+990 uL=1000 uL/1 mL of (0.01%) (1×)
  Dilute 20 uL of (1%)+980 uL=1000 uL/1 mL of (0.01%) (2×)
  Dilute 30 uL of (1%)+970 uL=1000 uL/mL of (0.01%) (3×)
  Dilute 40 uL of (1%)+960 uL=1000 uL, of (0.01%) (4×)
  Ergothioneine: 1 wt. % stock in distilled water (dH2O), filter-sterilized
  Dilute 10 uL of (1%)+990 uL=1000 uL/1 mL of (0.01%) (1×)
  Dilute 20 uL of (1%)+980 uL=1000 uL/1 mL of (0.01%) (2×)
  Dilute 30 uL of (1%)+970 uL=1000 uL/mL of (0.01%) (3×)
  Dilute 40 uL of (1%)+960 uL=1000 uL, of (0.01%) (4×)
  Niacinamide: 1 wt. % stock in dH2O, filter-sterilized
  Dilute 10 uL of (1%)+990 uL=1000 uL/1 mL of (0.01%) (1×)
  Dilute 20 uL of (1%)+980 uL=1000 uL/1 mL of (0.01%) (2×)
  Dilute 30 uL of (1%)+970 uL=1000 uL/mL of (0.01%) (3×)
  Dilute 40 uL of (1%)+960 uL=1000 uL, of (0.01%) (4×)
  $H_2O_2$: 3 wt. % stock in dH2O, filter-sterilized
  Dilute 10 uL of (1%)+990 uL=1000 uL/1 mL of (0.03%) (1×)
  Dilute 200 uL of (3%)+800 uL=1000 uL/1 mL of (0.3%) (2×)
  Dilute 300 uL of (3%)+700 uL=1000 uL/mL of (0.01%) (3×)
  Dilute 400 uL of (3%)+600 uL=1000 uL, of (0.01%) (4×)
  DMSO: 10 wt. % stock in cell culture media
  Dilute 10 uL (10% stock)+990 uL of cell culture media=1000 uL/1 mL of (0.1%) (1×)
  Dilute 20 uL (10% stock)+980 uL of media=1000 uL/1 mL (2×)

| | Types of treatment | Dilution | uLs /well |
|---|---|---|---|
| A | DMSO | 1X | 500 uL |
| B | α- tocopherol (0.01%) | 1X | 500 uL |
| C | Ergothioneine (EGT) (0.01%) | 1X | 500 uL |
| D | Niacinamide (0.01%) | 1X | 500 uL |
| E | α- tocopherol (0.01%) + EGT (0.01%) + Nicotinamide (0.01%) | 3X | 167 uL + 167 uL |
| F | DMSO + $H_2O_2$ (0.3%) | 2X | 250 uL + 250 uL |
| G | α- tocopherol (0.01%) + $H_2O_2$ (0.3%) | 2X | 250 uL + 250 uL |
| H | EGT (0.01%) + $H_2O_2$ (0.3%) | 2X | 250 uL + 250 uL |
| I | Niacinamide (0.01%) + $H_2O_2$ (0.3%) | 2X | 250 uL + 250 uL |
| J | α- tocopherol (0.01%) + EGT (0.01%) + Nicotinamide (0.01%) + $H_2O_2$ (0.3%) | 4X | 125 uL + 125 uL |

Cell Culture Treatment
  500 uL of each treatment sample was directly applied to the 24-well plates and incubated for 30 mins.
  Post incubation: each well was washed with the wash buffer (1×) provided.

250 uL of green Fluorescent (GF) dye containing media (2.5 uL of GF dye/250 uL of media) was then added to each well and incubate for 60 mins.

Post incubation, Fluorescence was read on a microplate reader at 490/525.

Test Products:

Test samples are listed in Table 6.

TABLE 6

| | Test Product (wt. %) | $H_2O_2$ (0.3 wt. %) | Description (wt. %) |
|---|---|---|---|
| A | DMSO | − | 0.1% + DMSO |
| F | DMSO | + | 0.1% + DMSO + 0.3% of $H_2O_2$ (0.3%) in untreated media |
| G | Alpha-tocopherol (0.01%) | + | Alpha-tocopherol (0.01%) + 0.3% of $H_2O_2$ (0.3%) in untreated media |
| H | EGT (0.01%) | + | EGT (0.01%) + 0.3% of $H_2O_2$ (0.3%) in untreated media |
| I | Niacinamide (0.01%) | + | Niacinamide (0.01%) + 0.3% of $H_2O_2$ (0.3%) in untreated media |
| J | Alpha-tocopherol (0.01%) + EGT (0.01%) + Niacinamide (0.01%) | + | Alpha-tocopherol (0.01%) + EGT (0.01%) + Niacinamide + 0.3% of $H_2O_2$ (0.3%) in untreated media |

Results:

0.3 wt. % $H_2O_2$ treatment results in a significant increase in ROS produced by the human derived keratinocytes.

0.01 wt. % of α-tocopherol+0.01% EGT+0.01% Niacinamide collective treatment on human derived keratinocyte culture results in greater than 36% decrease in ROS generated relative to the 0.3 wt. % of $H_2O_2$ treatment.

This decrease in ROS by combinatorial treatment of the three compounds is significantly greater than the decrease observed by individual treatment by 0.01 wt. % of α-tocopherol, 0.01 wt. % EGT and 0.01 wt. % Niacinamide, respectively.

Experiments were performed in three replicas. The results are shown in Tables 7 and 8 below.

TABLE 7

Significant Decrease in ROS generated in keratinocyte by antioxidant treatment (Fold Change (relative to untreated))

| | Treatment | P Values | Fold Change |
|---|---|---|---|
| A vs F | DMSO vs. 0.1% of DMSO + 0.3% $H_2O_2$ in untreated media | ** p < 0.0025 | 1.5-fold increase |
| F vs G | 0.1% of DMSO + 0.3% $H_2O_2$ in untreated media vs. Alpha-tocopherol (0.001%) | *p < 0.0139 | 0.4-fold decrease |
| F vs H | 0.1% of DMSO + 0.3% $H_2O_2$ in untreated media vs. EGT (0.01%) | Not significant | 0.31-fold decrease |
| F vs I | 0.1% of DMSO + 0.3% $H_2O_2$ in untreated media vs. Niacinamide (0.01%) | Not significant | 0.24-fold decrease |
| F vs J | 0.1% of DMSO + 0.3% $H_2O_2$ in untreated media vs. Alpha-tocopherol (0.001%) + EGT (0.01%) + Niacinamide (0.01%) | **p < 0.0038 | 0.54-fold decrease |

TABLE 8

Decrease in ROS generated in keratinocyte by antioxidant treatment

| | Treatment | $H_2O_2$ (0.3 wt. %) | % Decrease |
|---|---|---|---|
| A | DMSO | − | 33.33% |
| F | DMSO vs. 0.1% of DMSO + 0.3% $H_2O_2$ in untreated media | + | 0% |
| G | Alpha-tocopherol (0.001%) | + | 20.79% |
| H | EGT (0.01%) | + | 15.91% |
| I | Na PCA (0.01%) | + | 25.75% |
| J | Alpha-tocopherol (0.001%) + EGT (0.01%) + Niacinamide (0.01%) | + | 36.13% |

The results demonstrate that a combination of α-tocopherol, ergothioneine (EGT), and niacinamide provided a significant decrease in ROS production in human derived keratinocyte cell culture. This combination also shows an unexpected impact in decreasing ROS production in keratinocytes (treated with 0.3 wt. % hydrogen peroxide) relative to each treatment alone.

Example 4—Comparison of Various Ratios of Alpha-Tocopherol, EGT, Niacinamide

In further experiments various weight ratios of alpha-tocopherol to EGT to niacinamide (alpha-tocopherol:EGT:niacinamide) were tested to determine efficacy in reducing ROS production in human derived keratinocyte cell culture. The weight ratio of 1:1:3 for alpha-tocopherol to EGT to niacinamide (alpha-tocopherol:EGT:niacinamide) showed an unexpected enhancement in decreasing ROS production in keratinocytes (treated with 0.3 wt. % hydrogen peroxide) relative to other ratios of the same ingredient combination, including 1:1:1 (alpha-tocopherol:EGT:niacinamide).

Solutions with various ratios of Alpha-tocopherol:EGT:Niacinamide were tested in in-vitro studies conducted in a human derived keratinocyte cell culture model. Keratinocytes were treated with exogenous 0.3 wt. % hydrogen peroxide to induce ROS production.

Stock Solutions:
1 wt. % α-tocopherol, was prepared by dissolving 10 uL of α-tocopherol (100%) in 990 uL of DMSO (100%).
1 wt. % niacinamide was prepared by dissolving in deionized water at 10 mg/mL, followed by filter sterilization.
1 wt. % ergothioneine was prepared by dissolving 10 uL of BioYouth EGT in 990 uL of deionized water followed by filter sterilization.
3 wt. % $H_2O_2$ was prepared by dissolving 100 uL of $H_2O_2$ (30%) in 900 uL of deionized water.
10 wt. % of DMSO was prepared by dissolving 100 uL DMSO (stock 100%)+900 uL cell culture media.

Dilutions

α-tocopherol: 1 wt. % stock in DMSO, filter-sterilized.
Dilute 10 uL of (1%)+990 uL=1000 uL/mL of (0.01%).
Niacinamide: 1 wt. % stock in distilled water (dH2O), filter-sterilized.
Dilute 10 uL of (1%)+990 uL=1000 uL/mL of (0.01%).
Ergothioneine: 1 wt. % stock in dH2O, filter-sterilized.
Dilute 10 uL of (1%)+990 uL=1000 uL/mL of (0.01%).
H2O2: 3 wt. % stock in dH2O, filter-sterilized.
Dilute 100 uL of (3%)+900 uL=1000 uL/1 mL of (0.3%).
The evaluated plate layout, which had different ratios of components is shown in Table 9, below.

TABLE 9

| Untreated (400 uL of media) | Untreated (400 uL of media) | Untreated (400 uL of media) | 0.3 wt. % H2O2 (400 uL of 0.3% H₂O₂) | 0.3 wt. % H2O2 (400 uL of 0.3% H₂O₂) | 0.3 wt. % H2O2 (400 uL of 0.3% H₂O₂) |
|---|---|---|---|---|---|
| 0.01 wt. % α tocopherol + EGT + Niacinamide 1:1:1 (100 uL each = 300 ul) + 0.3% H2O2 (100 ul) | 0.01 wt. % α tocopherol + EGT + Niacinamide 1:1:1 (100 uL each = 300 ul) + 0.3% H2O2 (100 ul) | 0.01 wt. % α tocopherol + EGT + Niacinamide 1:1:1 (100 uL each = 300 ul) + 0.3% H2O2 (100 ul) | 0.01 wt. % α tocopherol + EGT + Niacinamide 1:2:1 (75 uL:150 uL:75 uL) = 300 uL + 0.3% H2O2 (100 ul) | 0.01 wt. % α tocopherol + EGT + Niacinamide 1:2:1 (75 uL:150 uL:75 uL) = 300 uL + 0.3% H2O2 (100 ul) | 0.01 wt. % α tocopherol + EGT + Niacinamide 1:2:1 (75 uL:150 uL:75 uL) = 300 uL + 0.3% H2O2 (100 ul) |
| 0.01 wt. % α tocopherol + EGT + Niacinamide 2:1:1 (150 uL:75 uL:75 uL) = 300 uL + 0.3% H2O2 (100 ul) | 0.01 wt. % α tocopherol + EGT + Niacinamide 2:1:1 (150 uL:75 uL:75 uL) = 300 uL + 0.3% H2O2 (100 ul) | 0.01 wt. % α tocopherol + EGT + Niacinamide 2:1:1 (150 uL:75 uL:75 uL) = 300 uL + 0.3% H2O2 (100 ul) | 0.01 wt. % α tocopherol + EGT + Niacinamide 1:1:2 (75 uL:75 uL:150 uL) = 300 uL + 0.3% H2O2 (100 ul) | 0.01 wt. % α tocopherol + EGT + Niacinamide 1:1:2 (75 uL:75 uL:150 uL) = 300 uL + 0.3% H2O2 (100 ul) | 0.01 wt. % α tocopherol + EGT + Niacinamide 1:1:2 (75 uL:75 uL:150 uL) = 300 uL + 0.3% H2O2 (100 ul) |
| 0.01 wt. % α tocopherol + EGT + Niacinamide 3:1:1 (180 uL:60 uL:60 uL) = 300 uL + 0.3% H2O2 (100 ul) | 0.01 wt. % α tocopherol + EGT + Niacinamide 3:1:1 (180 uL:60 uL:60 uL) = 300 uL + 0.3% H2O2 (100 ul) | 0.01 wt. % α tocopherol + EGT + Niacinamide 1:3:1 (60 uL:180 uL:60 uL) = 300 uL + 0.3% H2O2 (100 ul) | 0.01 wt. % α tocopherol + EGT + Niacinamide 1:3:1 (60 uL:180 uL:60 uL) = 300 uL + 0.3% H2O2 (100 ul) | 0.01 wt. % α tocopherol + EGT + Niacinamide 1:1:3 (60 uL:60 uL:180 uL) = 300 uL + 0.3% H2O2 (100 ul) | 0.01 wt. % α tocopherol + EGT + Niacinamide 1:1:3 (60 uL:60 uL:180 uL) = 300 uL + 0.3% H2O2 (100 ul) |

TABLE 10

Decrease in ROS generated in keratinocyte by antioxidant treatment

| Treatment | Fold Change (relative to untreated) |
|---|---|
| Untreated | 1 |
| 0.3% $H_2O_2$ in untreated media | 2.3-fold increase |
| 1:1:1 (Alpha-tocopherol:EGT:Niacinamide) | 1.4-fold decrease |
| 2:1:1 ((Alpha-tocopherol:EGT:Niacinamide) | 1.4-fold decrease |
| 1:2:1 ((Alpha-tocopherol:EGT:Niacinamide) | 1.45-fold decrease |
| 1:1:2 ((Alpha-tocopherol:EGT:Niacinamide) | 1.47-fold decrease |
| 1:3:1 ((Alpha-tocopherol:EGT:Niacinamide) | 1.46-fold decrease |
| 3:1:1 ((Alpha-tocopherol:EGT:Niacinamide) | 1.39-fold decrease |
| 1:1:3 ((Alpha-tocopherol:EGT:Niacinamide) | 1.57-fold decrease |

Example 5—Combinations with Alpha-Tocopherol, Ergothioneine and Niacinamide and UV Protection Exposure to UV radiation can cause an increase in photolesions in the form of thymine dimers. For example, due to exposure to UV radiations adjacent thymine residues can become linked covalently resulting in dimers. These dimers can be replicated as a single base causing mutations. Additionally, exposure to UV radiations can possibly decrease enzymes such as catalase. Catalase is believed to convert reactive oxygen species such as hydrogen peroxide to water and oxygen, reducing its toxic effects. Additionally, exposure to UV is believed to possibly decrease skin barrier protein (such as loricrin) and extracellular matrix proteins (such as collagen).

The outermost layer, epidermis of the skin, serves the function of forming a protective barrier against external environmental stresses, chemical damage and bacterial infection. The skin barrier comprises a number of proteins including Loricrin. Loricrin is a major protein present in the terminally differentiated cornified envelope and contributes to the protective barrier function of the stratum corneum.

The extracellular matrix (ECM) is composed of a number of different macromolecules including collagen, elastin, fibronectin and laminin, all believed to be organized in a tissue-specific manner. These protein components link together to form structurally stable tissue supporting structures.

In these Examples, Genoskin human skin explants were either 1) left untreated; 2) exposed to UV (A+B) at 20 J/cm2); 3) treated with placebo followed by UV exposure; or 4) treated with a mixture of alpha-tocopherol, ergothioneine (EGT) and niacinamide, in a weight ratio of alpha-tocopherol to EGT to niacinamide of 1:1:3 ratio, followed by UV exposure. Changes in the number of thymine dimer-positive cells/field of view, the amount of catalase expression, the fold changes in loricrin and extracellular matrix protein collagen expression were measured for each treatment.

From the data, the combined mixture of alpha-tocopherol, ergothioneine (EGT), and niacinamide in a weight ratio of alpha-tocopherol to EGT to niacinamide of 1:1:3 is believed to benefit the skin by: decreasing mutation causing changes in skin cells, restoring protective enzymes in the skin, and helping barrier and extracellular matrix formation to mimic that of untreated/nascent skin.

Method:

Tissue Treatment:

In vitro studies were conducted using Genoskin human skin explants. The skin explants were first normalized at least one hour before treatments with 1 mL media and incubated at a temperature of 37° C. with 5% $CO_2$ before being left untreated, treated with placebo, or treated with a mixture of alpha-tocopherol, EGT, and niacinamide at a weight ratio of alpha-tocopherol to EGT to niacinamide of 1:1:3. The skin explants being treated with the placebo or mixture of alpha-tocopherol, EGT, and niacinamide received an application of the placebo or the mixture alpha-tocopherol, EGT, and niacinamide once a day for 5 days. On the sixth day, the skin explants receiving the treatment were then exposed to UVA+UVB at 20 J/cm2. Following the UV exposure, the tissue samples were then treated with either the placebo or the mixture and incubated for 24 hours at a temperature of 37° C. with 5% $CO_2$. The tissue samples were then collected for either RNA extraction and analysis or fixed with 4 wt. % PFA, followed by paraffin embedding processes.

Immunofluorescent Staining:

The PFA-fixed paraffin-embedded tissues were de-waxed by heat and xylene treatment followed by hydration of the tissue by a gradient of ethanol ranging from 100% to 50% followed by water. The tissue slides then go through the antigen retrieval step using citric acid-based solution (pH 6.0) for 30 minutes, during which tissue slides were immersed in the solution and heated using a commercially available hot plate stirrer. The tissue slides were then cooled down to a temperature of 60° C., and washed 1×PBS. Following this, the tissue samples were blocked for 1 hour 30 minutes at room temperature in PBS containing 5 wt. % goat serum and 0.1 wt. % triton ×100.

Primary antibody (anti-rabbit Catalase) incubations occurred overnight at a temperature of 4° C. Post primary antibody treatment, the tissue slides were washed in PBS and incubated with fluorescently labelled secondary antibody (Alexa Fluor 488 Dye, ThermoFisher Scientific, A11006, 1:1000) for 1 hour 30 minutes at room temperature. Following the secondary antibody treatment, the slides were washed with PBS followed by air-drying and mounting them with Prolong Gold antifade medium containing DAPI nuclear counterstain (vectashield antifade mounting media with DAPI) (vector laboratories, H1200). Images were collected by a microscope, EVOS FL Auto (Life technologies).

Immunohistochemistry and Thymine Dimer

The tissue sections were heated for 1 hour at a temperature of 60° C. followed by hydration with Xylene, 100%-30% Ethanol and deionized water. The tissue slides then go through the antigen retrieval step using citric acid-based solution (pH 6.0) for 30 minutes, during which the tissue slides were immersed in the solution and heated using a commercially available hot plate stirrer. The tissue slides were then cooled down to 60° C., and washed 1×PBS. Following this, the tissue samples were blocked for 1 hour 30 minutes at room temperature in PBS containing 5 wt. % goat serum and 0.1 wt. % triton ×100. For DNA denaturation: the tissue sections were placed in 2N HCl for 30 minutes at a temperature 37° C. followed by wash and hydrogen peroxide block: 3 wt. % hydrogen peroxide (1 mL 30% hydrogen peroxide+9 mL PBS) for 15 min at RT. Primary Antibody was then applied and incubated for 1 hour at room temperature (Thymine Dimer (mouse monoclonal 11192-1.5 ul in 1.5 mL) 1:1000). This was followed by a secondary antibody treatment of Biotinylated Universal Antibody incubated for 30 min at room temperature. RTU Vectastain Elite ABC Reagent was then applied and incubated for 30 min followed by ImmPACT NovaRED (5 mL Diluent, 3 drops #1, 2 drops #2, 2 drops #3, 2 drops #4) and incubate for 2-15 min, at room temperature, respectively. Finally, the tissues undergo counterstain with hematoxylin and mounting.

RT-QPCR:

RNA was extracted from RNAlater stabilized tissues using a homogenizer (Kinematica, Bohemia, NY) and RNeasy Plus Mini Kit (Qiagen) according to the manufacturer's protocol. Extracted RNAs was quantitated using NanoDrop One (ThermoFisher Scientific). Based on the RNA concentrations, cDNA synthesis was performed using Maxima First Strand cDNA Synthesis kit for RT-qPCR with dsDNase (ThermoFisher) and gene expression analysis was performed using Taqman™ array cards using QuantStudio 7 Flex (ThermoFisher). Forty-eight skin specific targets and endogenous controls were selected for analysis. Relative quantitations from treatments were calculated and compared to UV only samples or untreated. A t-test was used to evaluate statistical significance and p-value was corrected by Benjanmini-Hochberg false discovery rate using the Thermo Fisher Cloud app.

Reagents:

RNeasy Mini Kit (QIAGEN)

Thermo Scientific Maxima H Minus First Strand cDNA Synthesis Kit

TaqMan™ Fast Advanced Master Mix

Results:

The tissues were either untreated, treated with UV alone, treated with placebo following UV, or treated with the antioxidant mix of alpha-tocopherol, EGT, and niacinamide in a weight ratio of alpha-tocopherol to EGT to niacinamide of 1:1:3 followed by UV. Post the one week treatment, the tissues were fixed and sectioned and immunohistochemically labeled with an antibody against a thymine dimer.

The results demonstrated that with UV light treatment there was a significant increase in thymine dimer positive cells in tissues. However, the antioxidant mixture treatment exhibited a significant reduction in the effect of UV on the tissues. Data is presented in Table 11 and FIG. 1.

TABLE 11

| Treatment | Average number of thymine dimer positive cells relative to the field of view |
|---|---|
| Untreated | 0 |
| Untreated + UV Light | 43.6 * |
| Placebo | 22.4 |
| Alpha-tocopherol + EGT + Niacinamide (1:1:3)*** | 3.8 ** |

* $p < 0.001$ vs. "untreated"
** $p < 0.001$ vs. "untreated + UV Light"
***Based on raw material weights.

Figure 2A:
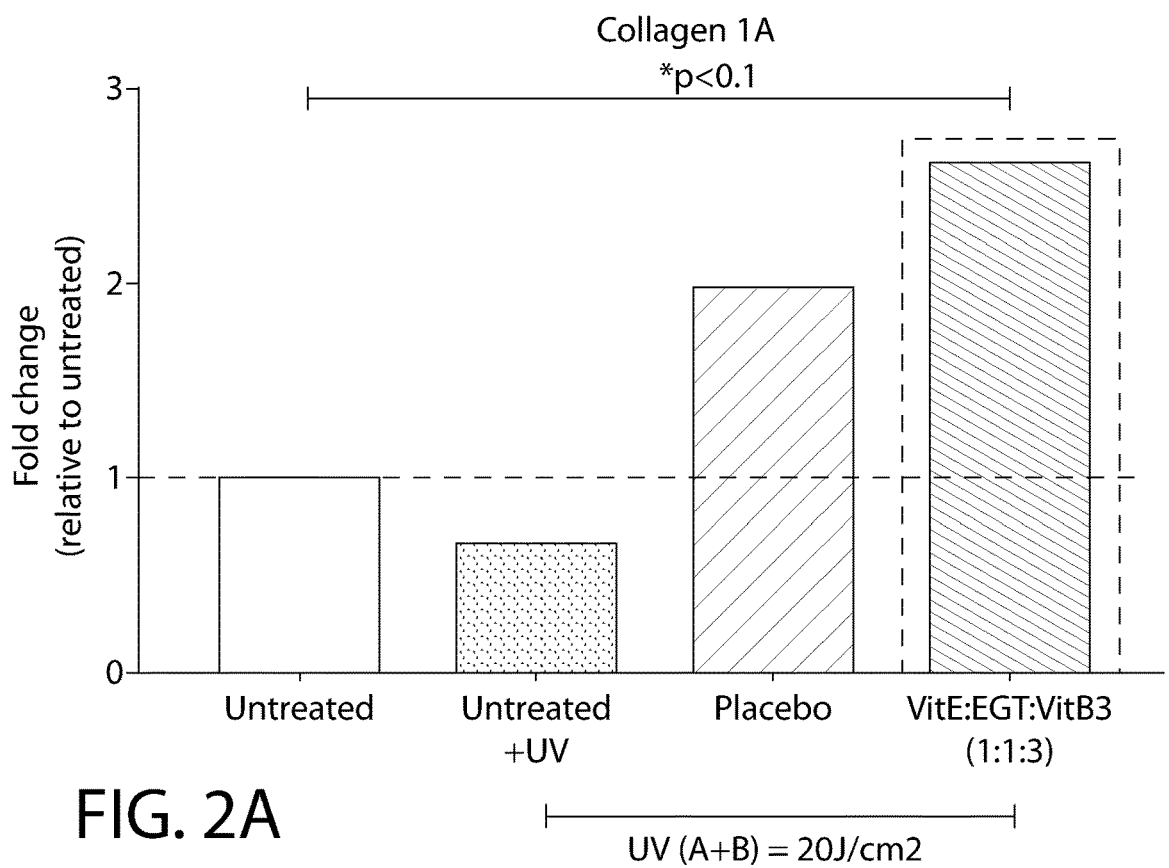
FIGS. 2A and 2B are bar graphs depicting the collagen production after application of a non-limiting exemplary compositions and exposure to UV in accordance with an aspect of the invention.
Figure 2B:
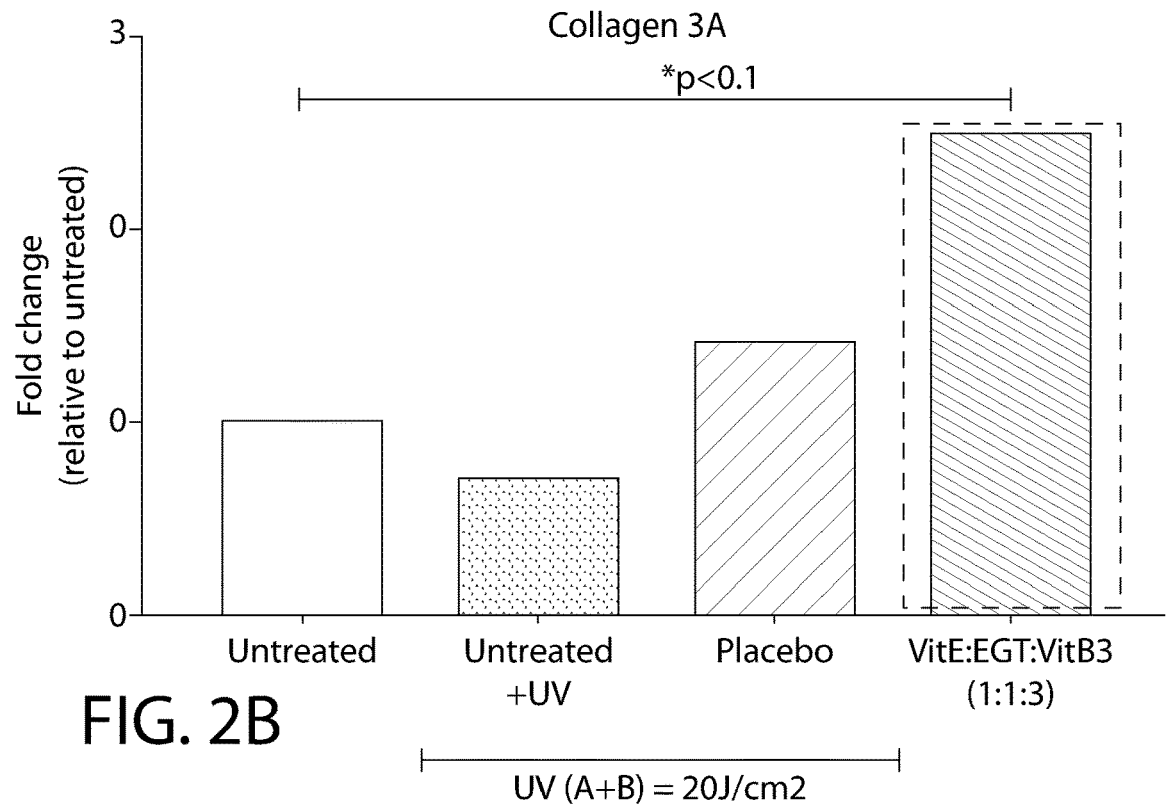
Figure 3:
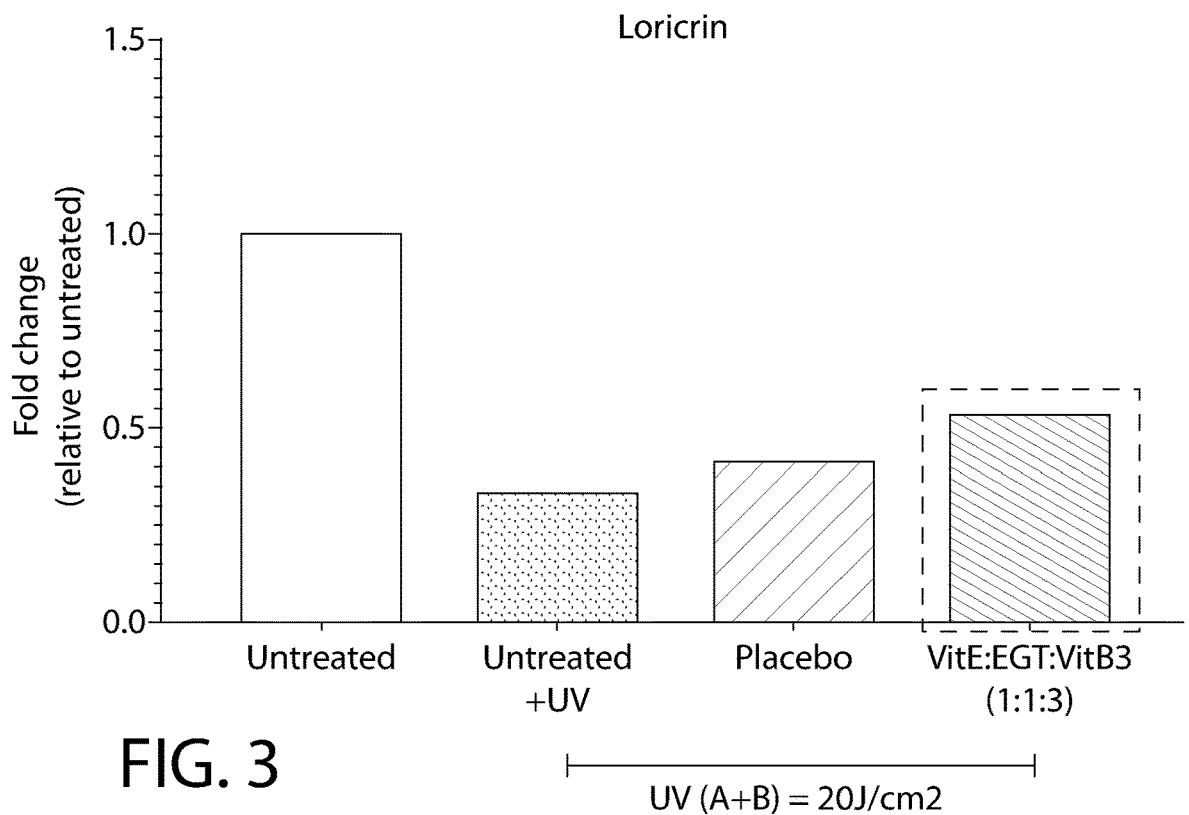
FIG. 3 is a bar graph depicting the loricrin production after application of a non-limiting exemplary compositions and exposure to UV in accordance with an aspect of the invention.

The tissues were either untreated, treated with UV alone, treated with placebo followed by UV light or treated with the antioxidant mix followed by UV light. After a one week treatment, the tissues were collected and their RNA extracted followed by cDNA synthesis. Quantitative Real Time PCR (qRT-PCR) was performed to evaluate changes in the genetic expression of Extracellular matrix protein, such as Collagen (Col1A and Col3A), and skin barrier proteins (loricrin). A summary of the results are presented in Tables 12, 13, and 14 and FIGS. 2A, 2B, and 3.

TABLE 12

| Collagen 1A expression | |
|---|---|
| Treatment | Fold Change Relative to Untreated |
| Untreated | 1 |
| Untreated + UV Light | 0.688 |
| Placebo | 1.985 |
| Alpha-tocopherol + EGT + Niacinamide (1:1:3)* | 2.635 |

TABLE 13

Collagen 3A expression

| Treatment | Fold Change Relative to Untreated |
|---|---|
| Untreated | 1 |
| Untreated + UV Light | 0.729 |
| Placebo | 1.428 |
| Alpha-tocopherol + EGT + Niacinamide (1:1:3)* | 2.52 |

TABLE 14

Loricrin expression

| Treatment | Fold Change Relative to Untreated |
|---|---|
| Untreated | 1 |
| Untreated + UV Light | 0.337 |
| Placebo | 0.412 |
| Alpha-tocopherol + EGT + Niacinamide (1:1:3)* | 0.539 |

The tissues were either untreated, treated with UV alone, treated with placebo followed by UV light or treated with the antioxidant mix followed by UV light. Post the one-week treatment, the tissues were fixed and sectioned and immunohistochemically labeled with an antibody against catalase. For the UV treatment tissues, there was a significant decrease in catalase expression in tissues. However, the antioxidant mixture (alpha-tocopherol, EGT, and niacinamide) treatment provided a significant decrease in the effect of UV light on the tissues. A summary of the results from the immunohistochemistry labelling are described in Table 15.

TABLE 15

Immunofluorescent Staining and Catalase Expression

| Treatment | Mean grey intensity of catalase expression |
|---|---|
| Untreated | 14.7 |
| Untreated + UV Light | 11.7 |
| Placebo | 10.6 |
| Alpha-tocopherol + EGT + Niacinamide (1:1:3)* | 18.7 |

Example 5

Non-limiting, example skin care compositions (Example Compositions E-H) were prepared according to aspects of the disclosure. The formulation for Example Compositions E-H are shown in Table 16.

TABLE 16

| US INCI Compound Name | Ex. E (wt. %) | Ex. F (wt. %) | Ex. G (wt. %) | Ex. H (wt. %) |
|---|---|---|---|---|
| Niacinamide | 0.408 | 2 | 1 | 2 |
| Taurine | 0.265 | 1.3 | 0.65 | 1.3 |
| Carnosine | 0.204 | 1 | 0.5 | 1 |
| PCA | 0.204 | 1 | 0.5 | 1 |
| Arginine | 0.139 | 0.68 | 0.34 | 0.68 |
| Hydrolyzed Hyaluronic acid | 0.051 | 1 | 0.5 | 1 |
| Glycine | 0.004 | 0.02 | 0.01 | 0.02 |
| Magnesium Sulfate | 0.002 | 0.01 | 0.005 | 0.01 |

TABLE 16-continued

| US INCI Compound Name | Ex. E (wt. %) | Ex. F (wt. %) | Ex. G (wt. %) | Ex. H (wt. %) |
|---|---|---|---|---|
| Nicotinamide Adenine Dinucleiotide | 0.002 | 0.01 | 0.005 | 0.01 |
| EGT | 0.001 | 0.005 | 0.0025 | 0.005 |
| Tocopherol | 0.2 | 0.5 | 0.5 | 1 |
| Encapsulation (made by Effervescence) | 0.8 | 0.8 | 0.8 | 0.8 |
| Water | 8.21 | 1 | 0.5 | 1 |
| Mannitol | 0.203 | 0.995 | 0.4975 | 0.995 |
| Pentylene glycol | 0.15 | | | |
| Citric acid | 0.13 | | | |
| Sodium Benzoate | 0.016 | | | |
| Benzoic acid | 0.01 | | | |
| BASE | 89.001 | 89.68 | 94.19 | 89.18 |

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

What is claimed is:

1. A skin care composition comprising:
   from about 0.1 to about 3 wt. % of vitamin E comprising alpha-tocopherol;
   from about 0.1 to about 7 wt. % of an amino acid component, the amino acid component comprising ergothioneine;
   wherein the amino acid component further comprises taurine, arginine, and glycine; and
   from about 0.7 to about 5 wt. % of vitamin B comprising niacinamide,
   wherein the skin care composition has a weight ratio of the taurine to the arginine to the glycine (taurine:arginine:glycine) from about 85:45:1 to about 45:24:1, and
   wherein all weight percentages are based on the total weight of the skin care composition.

2. The skin care composition according to claim 1, wherein the skin care composition has a weight ratio of alpha-tocopherol to ergothioneine of about 6:1 to about 1:6.

3. The skin care composition according to claim 1, wherein the skin care composition has a weight ratio of alpha-tocopherol to niacinamide of from about 1:1 to about 1:11.

4. The skin care composition according to claim 1, wherein the skin care composition has a weight ratio of ergothioneine to niacinamide of from about 1:1 to about 1:11.

5. The skin care composition according to claim 1, further comprising carnosine in an amount from about 0.1 to 5 wt. %.

6. A skin care composition comprising:
   from about 0.1 to about 3 wt. % of vitamin E comprising alpha-tocopherol;
   from about 0.7 to about 5 wt. % of vitamin B comprising niacinamide,
   at least one of an amino acid component comprising ergothioneine or a pyrrolidone carboxylic acid and/or a salt thereof, wherein the amino acid component further comprises taurine, arginine, and glycine, wherein the skin care composition has a weight ratio of the taurine to the arginine to the glycine (taurine:arginine:glycine) from about 85:45:1 to about 45:24:1, and wherein all weight percentages are based on the total weight of the skin care composition.

7. The skin care composition according to claim 6 further comprising:

hyaluronic acid; and from 0.5 to 5 wt. % of ascorbyl glucoside.

8. The skin care composition according to claim 6, further comprising carnosine in an amount from about 0.1 to 5 wt. %.

9. The skin care composition according to claim 7, wherein the hyaluronic acid has a molecular weight of about 300 kDa or less.

10. The skin care composition according to claim 6 further comprising astaxanthin from 0.001%-0.05% by wt. of the composition.

\* \* \* \* \*